US012740966B2

(12) United States Patent
Chen et al.

(10) Patent No.: US 12,740,966 B2
(45) Date of Patent: Sep. 22, 2026

(54) METHOD FOR IMPROVING BIOAVAILABILITY OF NAD+ DERIVATIVES

(71) Applicant: HOBOOMLIFE BIO-TECHNOLOGY (SHENZHEN) CO., LTD., Shenzhen (CN)

(72) Inventors: Jiansheng Chen, Shenzhen (CN); Yaying Hou, Shenzhen (CN); Tong Zhang, Shenzhen (CN); Jing Lyu, Shenzhen (CN); Yuqin Bai, Shenzhen (CN)

(73) Assignee: HOBOOMLIFE BIO-TECHNOLOGY (SHENZHEN) CO., LTD., Shenzhen (CN)

( * ) Notice: Subject to any disclaimer, the term of this patent is extended or adjusted under 35 U.S.C. 154(b) by 353 days.

(21) Appl. No.: 18/467,740

(22) Filed: Sep. 15, 2023

(65) Prior Publication Data

US 2024/0139147 A1 May 2, 2024

(30) Foreign Application Priority Data

Oct. 27, 2022 (CN) ......................... 202211328092.7

(51) Int. Cl.

| | |
|---|---|
| ***A61K 31/352*** | (2006.01) |
| ***A61K 9/51*** | (2006.01) |
| ***A61K 31/05*** | (2006.01) |
| ***A61K 31/455*** | (2006.01) |
| ***A61K 36/185*** | (2006.01) |
| ***A61K 36/73*** | (2006.01) |
| ***A61K 36/87*** | (2006.01) |
| ***A61P 3/00*** | (2006.01) |

(52) U.S. Cl.

CPC .......... *A61K 31/352* (2013.01); *A61K 9/5161* (2013.01); *A61K 31/05* (2013.01); *A61K 31/455* (2013.01); *A61K 36/185* (2013.01); *A61K 36/73* (2013.01); *A61K 36/87* (2013.01); *A61P 3/00* (2018.01)

(58) Field of Classification Search

CPC .... A61K 31/352; A61K 9/5161; A61K 31/05; A61K 31/455; A61K 36/185; A61K 36/73; A61K 36/87; A61K 9/1652; A61K 9/20; A61K 31/706; A61K 36/889; A61K 9/167; A61K 9/1623; A61K 9/1635; A61K 9/1682; A61K 31/7084; A61K 45/06; A61P 3/00; A61P 3/04; A61P 3/10; A61P 9/10; A61P 25/28; A61P 37/02; A61P 39/00

See application file for complete search history.

(56) References Cited

U.S. PATENT DOCUMENTS

| | | | |
|---|---|---|---|
| 2003/0148992 A1 | 8/2003 | Block et al. | |
| 2005/0181044 A1 | 8/2005 | Romero | |
| 2021/0008010 A1* | 1/2021 | Nandra ..................... | A61P 1/00 |
| 2021/0015788 A1 | 1/2021 | Conlon et al. | |
| 2021/0077514 A1* | 3/2021 | Vora ................... | A61K 31/4375 |
| 2021/0369751 A1 | 12/2021 | Park | |

FOREIGN PATENT DOCUMENTS

| | | | |
|---|---|---|---|
| CN | 109475572 A | 3/2019 | |
| CN | 112089705 A * | 12/2020 | ........... A61K 9/5042 |
| CN | 112137977 A | 12/2020 | |
| CN | 114762732 A * | 7/2022 | ........... A61K 48/005 |
| WO | WO-2019175587 A1 * | 9/2019 | .............. A61P 37/00 |
| WO | 2021247776 A1 | 12/2021 | |
| WO | 2022172225 A1 | 8/2022 | |

OTHER PUBLICATIONS

CN-114762732-A, Translation, 16 pages. (Year: 2022).*
CN-112089705-A, Translation, 9 pages. (Year: 2020).*
He, H., Zhang, Q., Li, M., Wang, J., Mei, X., Modulating the Dissolution and Mechanical Properties of Resveratrol by Cocrystallization, 2017, Crystal Growth & Design, 17(7):3989-3996, 8 pages. DOI: 10.1021/acs.cgd.7b00637. (Year: 2017).*
Wu N, Zhang Y, Ren J, Zeng A, Liu J. Preparation of quercetin-nicotinamide cocrystals and their evaluation under in vivo and in vitro conditions. RSC Adv. Jun. 9, 2020;10(37):21852-21859, 8 pages. doi: 10.1039/d0ra03324c. PMID: 35516602; PMCID: PMC9054514. (Year: 2020).*
The Grant Notice from corresponding Chinese Application No. 202211328092.7, dated Mar. 24, 2023. English translation attached.
Tarrago, MG et al."A Potent and Specific CD38 Inhibitor Ameliorates Age-Related Metabolic Dysfunction by Reversing Tissue NAD+ Decline" Cell Metabolism , vol. 27,No. 5,May 1, 2018.
Chini, CCS et al."CD38 ecto-enzyme in immune cells is induced during aging and regulates NAD+ and NMN levels" Nature Metabolism , vol. 2,No. 11,Nov. 30, 2020.

(Continued)

*Primary Examiner* — Aaron J Kosar
*Assistant Examiner* — Jennifer Lynn Cain

(57) ABSTRACT

The present disclosure provides a method for improving bioavailability of an NAD+ derivative. The method improves the bioavailability of the NAD+ derivative by arranging a CD38 inhibitor and the NAD+ derivative in a same preparation, and controlling the CD38 inhibitor to release first rapidly, and then the NAD+ derivative releases after the CD38 inhibitor has taken effect, thereby increasing the level of NAD+ in vivo.

7 Claims, 6 Drawing Sheets

(56) References Cited

OTHER PUBLICATIONS

Grant Notice & Supplementary Search dated Oct. 21, 2024 received in Chinese Application No. CN202310413132.6. English translation attached.
First Office Action dated Apr. 3, 2024 received in corresponding patent family application No. CN202310413132.6. English translation attached.
Chen, Zhe et al. "Synthesis and Biological Evaluation of Nicotinamide Adenine Dinucleotides Analogues as Inhibitors of CD38", Chemical Journal of Chinese Universities, Dec. 31, 2012, p. 1226-1232. English translation attached.

* cited by examiner

METHOD FOR IMPROVING BIOAVAILABILITY OF NAD+ DERIVATIVES

CROSS-REFERENCE TO RELATED APPLICATIONS

This application claims priority to Chinese Patent Application No. 202211328092.7, filed with the China National Intellectual Property Administration on Oct. 27, 2022, and entitled "MICROSPHERE PREPARATION FOR EFFICIENTLY IMPROVING NAD+ LEVEL AND PREPARATION PROCESS THEREOF", the entire content of which is incorporated herein by reference.

FIELD

The present disclosure relates to the technical field of medicines, and specifically, to a method for improving the bioavailability of an NAD+ derivative.

BACKGROUND

NAD+, whose full name is oxidized nicotinamide adenine dinucleotide, is found in all living cells and is a coenzyme of many dehydrogenases. It may transfer $H^+$ and electrons through a pyridine ring in a nicotinamide moiety, and play a vital role in the process of the tricarboxylic acid cycle (a key step in glucose metabolism). NAD+ is also the only ADP ribose donor in the body, and an essential substance to activate enzymes that maintain multiple life activities, such as Sirtuins (a highly conserved histone deacetylase family), PARPs (DNA repair enzymes), CD38, and CD157. Therefore, NAD+ is crucial in maintaining cellular energy metabolism, DNA damage repair, immune regulation, and other aspects. Studies have found that the level of NAD+ decreases steadily with age, resulting in the change of metabolism and the increase of disease susceptibility, and that restoring the level of NAD+ in an old or diseased animal can promote health and prolong lifespan. Preclinical studies have shown that NMN has multiple pharmacological effects on heart and cerebral ischemia, Alzheimer's disease, and type 2 diabetes caused by diet and age, and obesity, and these diseases are all related to the deficiency of NAD+.

Currently, co-use of a CD38 inhibitor and nicotinamide mononucleotide (NMN) can increase the level of NAD+ in HEK293T cells. However, certain incubation time is required for the CD38 inhibitor to achieve its NAD+ hydrolase inhibiting activity, and before CD38 is sufficiently inhibited, large amounts of NMN and NAD+ are still consumed by CD38.

Therefore, how to improve the level of NAD+ more efficiently remains to be further studied.

SUMMARY

The present disclosure aims to solve at least one of the technical problems in the prior art at least to a certain extent.

NMN, whose full name is nicotinamide mononucleotide, is a derivative of NAD+, is found in some fruits and vegetables and poultry meat, and is a naturally occurring substance in the human body. NMN is mainly used as an intermediate for biologically synthesizing the important coenzyme NAD+ in the human body, and NMN supplementation has been proved to enhance the biological synthesis of NAD+.

CD38 is a multi-functional enzyme and a main hydrolase of NAD+ and its precursors, and may metabolize NAD+, NMN, and NR into ADPR and cADPR. Removal of the CD38 gene may prevent age-associated NAD+ decrease and mitochondrial dysfunction. CD38 on the cell surface accounts for about 90% of total CD38 in the body. Therefore, exogenous NMN supplemented will be degraded by CD38 on the cell surface during the process of entering cells, which severely affects the utilization efficiency of NMN supplementation to improve NAD+.

In order to improve bioavailability of NMN and accordingly increase the level of NAD+ more efficiently, the inventors, after continuous innovation and experimentation, have proposed a method for increasing the level of NAD+ more efficiently by using a stepwise release of a CD38 inhibitor and NMN. In the method, the CD38 inhibitor and NMN are arranged in a same preparation, the CD38 inhibitor is first released rapidly, and then NMN is released after the CD38 inhibitor has taken effect, thus significantly improving the bioavailability of NMN. Through the preparation design, the present disclosure optimizes a rate and a time difference of the stepwise release of the CD38 inhibitor and NMN and achieves subsequent release of NMN after the CD38 is sufficiently inhibited, significantly improving the efficiency of co-use of the CD38 inhibitor and NMN.

In an aspect of the present disclosure, the present disclosure provides a microsphere. According to embodiments of the present disclosure, the microsphere includes a pellet core containing an NAD+ derivative and a coating containing a CD38 inhibitor, wherein an outer surface of the pellet core is wrapped with the coating. The inventors have found that stepwise release can be achieved by using the CD38 inhibitor as the coating and using the NAD+ derivative as the pellet core. In addition, the CD38 inhibitor coating is released rapidly in vivo and inhibits the expression of CD38 in cells. After an optimal time period when the CD38 inhibitor inhibits CD38 in vivo, the NAD+ derivative pellet core is released, which can be utilized by cells to the greatest extent, and the level of NAD+ in vivo can be increased efficiently.

According to the embodiments of the present disclosure, the foregoing microsphere may further include at least one of the following additional technical features.

According to the embodiments of the present disclosure, the CD38 inhibitor is selected from at least one of: quercetin, apigenin, resveratrol, grape seed extract, strawberry extract, and cocoa extract. The inventors have found that the foregoing CD38 inhibitors can inhibit the expression of cellular CD38 better.

It should be noted that quercetin or apigenin is mainly absorbed in the gastrointestinal tract in the human body, and the time from release to absorption of quercetin or apigenin is about 2 h-4 h. According to the embodiments of the present disclosure, the NAD+ derivative is selected from at least one of: nicotinamide mononucleotide (NMN), nicotinamide riboside (NR), nicotinamide (NAM), and nicotinamide adenine dinucleotide (NADH). The inventors have found that the foregoing NAD+ derivatives can promote the generation of NAD+ better.

According to the embodiments of the present disclosure, a mass ratio of the CD38 inhibitor to the NAD+ derivative is (0.5-30):(5-300). The inventors have found that stepwise release of the CD38 inhibitor and NMN within this mass ratio range can have an appropriate time difference, so that the utilization of the NAD+ derivative is further improved, and the content of NAD+ is significantly increased.

According to the embodiments of the present disclosure, the pellet core further contains an excipient for controlled release, and the coating further contains a filler.

According to the embodiments of the present disclosure, in the coating, a mass ratio of the CD38 inhibitor to the filler is 1:5 to 1:15. The inventors have found that the adoption of the CD38 inhibitor and the filler within this mass ratio range can endow the microsphere with a better shape, improve the stability of the microsphere, and control the release rate of the CD38 inhibitor.

According to a specific embodiment of the present disclosure, in the coating, the mass ratio of the CD38 inhibitor to the filler is 1:5 to 1:8.5 or 1:9 to 1:15.

According to a specific embodiment of the present disclosure, in the coating, the mass ratio of the CD38 inhibitor to the filler is 1:5 to 1:10 or 1:11.5 to 1:15. In the coating, the CD38 inhibitor and the filler within this mass ratio range can maximize the effect of increasing the level of NAD+.

It should be noted that the filler is selected from at least one of: glucose, sucrose, mannitol, xylitol, erythritol, and sodium bicarbonate.

It should be noted that in order to achieve a better quick-release effect of the CD38 inhibitor, a disintegrant may be further added in the coating to disintegrate the microsphere rapidly, so as to accelerate release of the CD38 inhibitor.

According to a specific embodiment of the present disclosure, the disintegrant is selected from at least one of: cross-linked povidone, low-substituted hydroxypropyl cellulose (L-HPC), cross-linked sodium carboxymethyl cellulose, dry starch, sodium carboxymethyl starch, cross-linked polyvinylpyrrolidone, and an effervescent disintegrant.

It should be noted that in order to endow the microsphere with a better shape and improve the stability of the microsphere, a binder may be further added in the coating.

According to a specific embodiment of the present disclosure, the binder is selected from at least one of: sodium carboxymethyl cellulose, povidone (K30), polyethylene glycol 6000, polyvinyl alcohol, polyurethane, and polystyrene.

According to the embodiments of the present disclosure, in the pellet core, a mass ratio of the NAD+ derivative to the excipient for controlled release is 5:1 to 5:10. The inventors have found that the adoption of the NAD+ derivative and the excipient within this mass ratio range can endow the microsphere with a better shape, improve the stability of the microsphere, and control the release rate of the NAD+ derivative.

According to a specific embodiment of the present disclosure, the mass ratio of the NAD+ derivative to the excipient for controlled release in the pellet core is 5:1 to 5:1.2 or 5:1.5 to 5:10.

According to a specific embodiment of the present disclosure, the mass ratio of the NAD+ derivative to the excipient for controlled release in the pellet core is 5:1 to 5:1.5 or 5:2 to 5:10. Among them, the NAD+ derivative to the excipient for controlled release within this mass ratio range can maximize the effect of increasing the level of NAD+.

It should be noted that in order to achieve a better slow-release effect of the NAD+ derivative, a foaming agent may be further added in the pellet core.

According to a specific embodiment of the present disclosure, the foaming agent is selected from at least one of: sodium bicarbonate, pine oil, cresol oil, terpineol, isobutyl methyl carbinol, methylpentanol, triethoxybutane, sodium alkylbenzene sulfonate, sodium alkyl sulfate, and polyethylene glycol ether.

According to the embodiments of the present disclosure, the excipient for controlled release is selected from at least one of: a hydrophilic gel material and a bioerodible material.

According to a specific embodiment of the present disclosure, the hydrophilic gel material is selected from at least one of: sodium carboxymethyl cellulose (CMC-Na), hydroxypropyl cellulose, hydroxypropyl methylcellulose (HPMC), povidone (PVP), ethyl cellulose (EC), polyethylene glycol, microcrystalline cellulose, carbomer (acrylic resin), alginate, and deacetylated chitosan (chitosan).

According to a specific embodiment of the present disclosure, the bioerodible material is selected from at least one of: beewax, carnauba wax, stearyl alcohol, glycerol monostearate, cetyl alcohol, stearyl alcohol, octacosanol, and rice bran fatty alkanol.

It should be noted that according to the embodiments of the present disclosure, if the hydrophilic gel material is used to prepare the microsphere, a weight ratio of the hydrophilic gel material in the entire microsphere is 5%-50%. If the bioerodible material is used to prepare the microsphere, a weight ratio of the bioerodible material in the entire microsphere is 3%-20%.

According to a specific embodiment of the present disclosure, the filler is selected from at least one of: glucose, sucrose, mannitol, xylitol, erythritol, and sodium bicarbonate.

According to the embodiments of the present disclosure, a mass ratio of the coating to the pellet core is (5-60):100. The inventors have found that the adoption of the coating and the pellet core within this mass ratio range can endow the microsphere with a better shape, and meanwhile, can allow the coating and the pellet core to be released at an appropriate time difference, so that the utilization of the NAD+ derivative is further improved and accordingly the level of NAD+ is increased.

According to the embodiments of the present disclosure, a time difference between a peak of the releasing of the CD38 inhibitor and the NAD+ derivative is at least 0.5 h. Within this time difference, when the CD38 inhibitor in the microsphere is released rapidly to inhibit CD38 in vivo to minimize CD38 activity in vivo, the NAD+ derivative in the microsphere is released slowly, so that the bioavailability of NAD+ derivative can be improved, the content of NAD+ derivative degraded by CD38 can be reduced, and accordingly the level of NAD+ can be increased.

According to a specific embodiment of the present disclosure, the time difference between a peak of the releasing of the CD38 inhibitor and the NAD+ derivative is 0.5 h-4 h, 0.5 h-2 h or 2 h-4 h.

According to a specific embodiment of the present disclosure, the time difference of release peak of the CD38 inhibitor and the NAD+ derivative is 0.5 h-1.5 h.

In another aspect of the present disclosure, the present disclosure provides a preparation method of the foregoing microsphere. According to embodiments of the present disclosure, the method includes: (1) performing a first mixing on a first excipient and an NAD+ derivative to obtain a pellet core; (2) performing a second mixing on a CD38 inhibitor and a second excipient; and (3) wrapping the surface of the pellet core with the second mixed product to obtain the microsphere. The inventors have found that stepwise release of the CD38 inhibitor and the NAD+ derivative can be achieved by the microsphere prepared by the method and thus improving the level of cellular NAD+.

According to the embodiments of the present disclosure, the foregoing method may further include at least one of the following additional technical features.

According to the embodiments of the present disclosure, the CD38 inhibitor is selected from at least one of: quercetin, apigenin, resveratrol, grape seed extract, strawberry extract, and cocoa extract. The inventors have found that the foregoing CD38 inhibitors can inhibit the expression of cellular CD38 better.

It should be noted that quercetin or apigenin is mainly absorbed in the gastrointestinal tract in the human body, and the time from release to absorption of quercetin or apigenin is about 2 h-4 h. Metabolic half-life of quercetin is 11 h-28 h, and metabolic half-life of apigenin is 91.8 h.

According to the embodiments of the present disclosure, the NAD+ derivative is selected from at least one of: nicotinamide mononucleotide (NMN), nicotinamide riboside (NR), nicotinamide (NAM), and nicotinamide adenine dinucleotide (NADH). The inventors have found that the foregoing NAD+ derivatives can promote the generation of NAD+ better.

According to the embodiments of the present disclosure, the first excipient includes an excipient for controlled release.

According to the embodiments of the present disclosure, the excipient for controlled release includes at least one selected from: a hydrophilic gel material and a bioerodible material.

According to a specific embodiment, the hydrophilic gel material is selected from at least one of: sodium carboxymethyl cellulose (CMC-Na), hydroxypropyl cellulose, hydroxypropyl methylcellulose (HPMC), povidone (PVP), ethyl cellulose (EC), polyethylene glycol, microcrystalline cellulose, carbomer (acrylic resin), alginate, and deacetylated chitosan (chitosan).

According to a specific embodiment of the present disclosure, the bioerodible material is selected from at least one of: beewax, carnauba wax, stearyl alcohol, glycerol monostearate, cetyl alcohol, stearyl alcohol, octacosanol, and rice bran fatty alkanol.

According to the embodiments of the present disclosure, the second excipient includes a filler.

According to a specific embodiment of the present disclosure, the filler is selected from at least one of: glucose, sucrose, mannitol, xylitol, erythritol, and sodium bicarbonate.

According to the embodiments of the present disclosure, the first excipient further includes a foaming agent.

According to a specific embodiment of the present disclosure, the foaming agent is selected from at least one of: sodium bicarbonate, pine oil, cresol oil, terpineol, isobutyl methyl carbinol, methylpentanol, triethoxybutane, sodium alkylbenzene sulfonate, sodium alkyl sulfate, and polyethylene glycol ether.

According to the embodiments of the present disclosure, the second excipient further includes a disintegrant.

According to a specific embodiment of the present disclosure, the disintegrant is selected from at least one of: cross-linked povidone, low-substituted hydroxypropyl cellulose (L-HPC), cross-linked sodium carboxymethyl cellulose, dry starch, sodium carboxymethyl starch, cross-linked polyvinylpyrrolidone, and an effervescent disintegrant. According to the embodiments of the present disclosure, when the pellet core is wrapped with the second mixed product, a third mixing is further performed on the second mixed product and a binder.

According to a specific embodiment of the present disclosure, the binder is selected from at least one of: sodium carboxymethyl cellulose, povidone (K30), polyethylene glycol 6000, polyvinyl alcohol, polyurethane, and polystyrene.

According to a specific embodiment of the present disclosure, a mass ratio of the CD38 inhibitor to the NAD+ derivative is (0.5-30):(5-300). The inventors have found that the adoption of the CD38 inhibitor and the NAD+ derivative within this mass ratio range can allow the CD38 inhibitor and NMN to be released step by step at an appropriate time difference, so that the utilization of the NAD+ derivative is further improved and accordingly the level of NAD+ is significantly increased.

According to a specific embodiment of the present disclosure, a mass ratio of the NAD+ derivative to the first excipient is 5:1 to 5:10. The inventors have found that the adoption of the NAD+ derivative and the first excipient within this mass ratio range can endow the microsphere with a better shape, improve the stability of the microsphere, and control the release rate of the NAD+ derivative.

According to a specific embodiment of the present disclosure, the mass ratio of the NAD+ derivative to the first excipient is 5:1 to 5:1.2 or 5:1.5 to 5:10.

According to a specific embodiment of the present disclosure, the mass ratio of the NAD+ derivative to the first excipient is 5:1 to 5:1.5 or 5:2 to 5:10. Among them, the NAD+ derivative and the first excipient within this mass ratio range can maximize the effect of increasing the level of NAD+.

It should be noted that the first excipient in "a mass ratio of the NAD+ derivative to the first excipient is 5:1 to 5:10" refers to an excipient for controlled release, and the foaming agent in the first excipient is an adjuvant and is nonessential.

According to a specific embodiment of the present disclosure, a mass ratio of the CD38 inhibitor to the second excipient is 1:5 to 1:15. The inventors have found that the adoption of the CD38 inhibitor and the second excipient within this mass ratio range can endow the microsphere with a better shape, improve the stability of the microsphere, and control the release rate of the CD38 inhibitor.

According to a specific embodiment of the present disclosure, the mass ratio of the CD38 inhibitor to the second excipient is 1:5 to 1:8.5 or 1:9 to 1:15.

According to a specific embodiment of the present disclosure, the mass ratio of the CD38 inhibitor to the second excipient is 1:5 to 1:10 or 1:11.5 to 1:15. Among them, the CD38 inhibitor and the second excipient within this mass ratio range can maximize the effect of increasing the level of NAD+ optimally.

It should be noted that the second excipient in "a mass ratio of the CD38 inhibitor to the second excipient is 1:5 to 1:15" refers to a filler, and the disintegrant in the excipient is an adjuvant and is nonessential.

According to a specific embodiment of the present disclosure, a mass ratio of the second mixed product to the pellet core is (5-60):100. The inventors have found that the adoption of the second mixed product and the pellet core within this mass ratio range can endow the microsphere with a better shape, and meanwhile, can allow the coating and the pellet core to be released at an appropriate time difference, so that the utilization of the NAD+ derivative is further improved and accordingly the level of NAD+ is increased.

According to a specific embodiment of the present disclosure, after the first mixing is performed on the first excipient and the NAD+ derivative, purified water is required for preparing a soft material, to uniformly mix the first excipient and the NAD+ derivative together.

According to the embodiments of the present disclosure, before the pellet core is wrapped with the second mixed product, drying the pellet core is further included. Excess water in the pellet core is removed, so that the pellet core can have a better shape and more stable properties.

According to a specific embodiment of the present disclosure, a weight ratio of water in the dried pellet core is 3%-5%.

According to a specific embodiment of the present disclosure, a diameter of the dried pellet core is 0.1 mm-0.2 mm.

According to a specific embodiment of the present disclosure, the wrapping is performed in a centrifugal granulator.

In another aspect of the present disclosure, the present disclosure provides a microsphere. According to the embodiments of the present disclosure, the microsphere is prepared by the foregoing method.

It should be noted that the all features and advantages described for the foregoing preparation method of the microsphere are also applicable to the microsphere, and will not be described in details here.

In another aspect of the present disclosure, the present disclosure provides use of the foregoing microsphere in preparation of a health product or medicine. According to embodiments of the present disclosure, the health product or medicine is used to increase the level of NAD+.

It should be noted that all features and advantages described for the foregoing microsphere are also applicable to the use, and will not be described in detail here.

In another aspect of the present disclosure, the present disclosure provides a method for increasing level of cellular NAD+. According to embodiments of the present disclosure, cells are exposed to a CD38 inhibitor and an NAD+ derivative successively. The cells are first exposed to the CD38 inhibitor, so that the content of cellular CD38 can be reduced to avoid degradation of the NAD+ derivative by CD38. Then, the cells are exposed to the NAD+ derivative, so that the bioavailability of the NAD+ derivative can be improved and accordingly the level of cellular NAD+ can be increased.

According to the embodiments of the present disclosure, the foregoing method may further include at least one of the following additional technical features.

According to the embodiments of the present disclosure, the cells are exposed to the CD38 inhibitor for a first contact treatment and, and the cells are exposed to the NAD+ derivative for a second contact treatment at least 0.5 h after the first contact treatment. Within the time difference, when the CD38 inhibitor inhibits CD38 in vivo to deactivate CD38 in vivo, the cells are exposed to the NAD+ derivative, so that bioavailability of the NAD+ derivative can be improved, the content of NAD derivative degraded by CD38 can be reduced, and accordingly the level of cellular NAD+ can be increased.

According to the embodiments of the present disclosure, the CD38 inhibitor is selected from at least one of: quercetin, apigenin, resveratrol, grape seed extract, strawberry extract, and cocoa extract. The inventors have found that the adoption of the foregoing CD38 inhibitors can inhibit the expression of cellular CD38 better.

According to the embodiments of the present disclosure, the NAD+ derivative is selected from at least one of: nicotinamide mononucleotide (NMN), nicotinamide riboside (NR), nicotinamide (NAM), and nicotinamide adenine dinucleotide (NADH). The inventors have found that the adoption of the foregoing NAD+ derivatives can promote the generation of NAD+ better.

According to the embodiments of the present disclosure, after the first contact treatment is performed for 0.5 h-4 h, 0.5 h-2 h, 0.5 h-1.5 h or 2 h-4 h, the cells are exposed to the NAD+ derivative for the second contact treatment. Within the time difference, when the CD38 inhibitor inhibits CD38 to deactivate CD38, the cells are exposed to the NAD+ derivative, so that bioavailability of the NAD+ derivative can be improved, the content of NAD derivative degraded by CD38 can be reduced, and accordingly the level of NAD+ can be increased.

According to the embodiments of the present disclosure, the CD38 inhibitor and the NAD+ derivative are provided in the form of a microsphere, and the microsphere is defined above.

In another aspect of the present disclosure, the present disclosure provides a method for increasing level of cellular NAD+. According to embodiments of the present disclosure, the foregoing microsphere is administered to the cells.

In another aspect of the present disclosure, the present disclosure provides a method for stepwise releasing of a CD38 inhibitor and an NAD+ derivative. According to embodiments of the present disclosure, the foregoing microsphere is used.

Additional aspects and advantages of the present disclosure will be given in the following description, and will be partially obvious from the following description or learned by practice of the present disclosure.

BRIEF DESCRIPTION OF DRAWINGS

The foregoing and/or additional aspects and advantages of the present disclosure will be obvious and easy to understand from the description of embodiments with reference to the following drawings.

DESCRIPTION OF EMBODIMENTS

Figure 1:
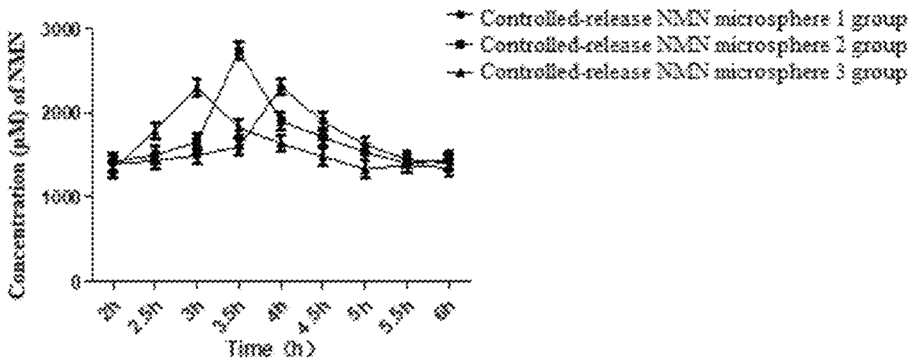
FIG. 1 is a diagram of a confirmatory experiment of release of NMN in controlled-release NMN microsphere 1, 2, and 3 groups according to an embodiment of the present disclosure.

Examples of the present disclosure will be described in detail below. The examples described below are exemplary and are used for explaining the present disclosure only, and should not be construed as limiting of the present disclosure. Experiments described in the examples without indicating specific technologies or conditions are carried out according to technologies or conditions described in documents in the art or according to product specifications. Reagents or instrument used without indicating manufacturers are all conventional products commercially available.

Example 1 Preparation of Controlled-Release NMN Microspheres with Different Ratios of Ingredients and Excipients 1. Preparation of a Controlled-Release NMN Microsphere 1:

(1) 150 g of NMN, 45 g of hydroxypropyl methylcellulose (an excipient for controlled release), 15 g of cetyl alcohol (an excipient for controlled release), and 20 g of sodium bicarbonate (a foaming agent) were taken and uniformly mixed, and the mixture was prepared into a soft material with purified water in a wet type granulator. The soft material was placed into an extrusion spheronizator and extruded, a sieve plate with the diameter of 0.2 mm was used, and the extruded pellets were rounded in the spheronizator and dried until the water content was 3%-5% of a mass concentration.

(2) 15 g of quercetin, 176 g of erythritol (a filler), and 54 g of cross-linked povidone (a disintegrant) were taken and uniformly mixed, the mixture was added to a powder feeding system of a centrifugal granulator, 5 g of sodium carboxymethyl cellulose (a binder) was taken and prepared into an aqueous solution with a mass concentration of 1% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

2. Preparation of a Controlled-Release NMN Microsphere 2:

(1) 200 g of NMN and 50 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and the extruded pellets were rounded in the spheronizator and dried until the water content was 3%-5% of a mass concentration.

(2) 20 g of quercetin, 172 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

3. Preparation of a Controlled-Release NMN Microsphere 3:

(1) 180 g of NMN, 20 g of sodium carboxymethyl cellulose (an excipient for controlled release), 20 g of hydroxypropyl methylcellulose (an excipient for controlled release), 20 g of ethyl cellulose (an excipient for controlled release), and 10 g of cross-linked povidone NF (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 18 g of quercetin, 200 g of xylitol (a filler), and 22 g of cross-linked carboxymethyl cellulose sodium (a disintegrant) were taken and uniformly mixed, the mixture was added to a powder feeding system of a centrifugal granulator, 10 g of polyethylene glycol 6000 (a binder) was taken and prepared into an aqueous solution with a mass concentration of 15% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 2 Confirmatory Experiment (Animal Experiment) of Release of Controlled-Release NMN Microspheres 12 SD rats weighing about 200 g were purchased, and an experiment was carried out after one week of adaptive feeding. The 12 rats were divided into 3 groups, 4 rats per group (half male and half female). The rats in group 1 were administered intragastrically with the controlled-release NMN microspheres 1, the rats in group 2 were administered intragastrically with the controlled-release NMN microspheres 2, and the rats in group 3 were administered intragastrically with the controlled-release NMN microspheres 3. Doses of NMN contained in the controlled-release NMN microspheres administered intragastrically to the rats in each groups were the same, and intragastric administration doses of NMN were all 100 mg/kg. Doses of quercetin contained in the controlled-release NMN microspheres administered intragastrically to the rats in each groups were the same, and intragastric administration doses of quercetin were all 10 mg/kg.

Figure 2:
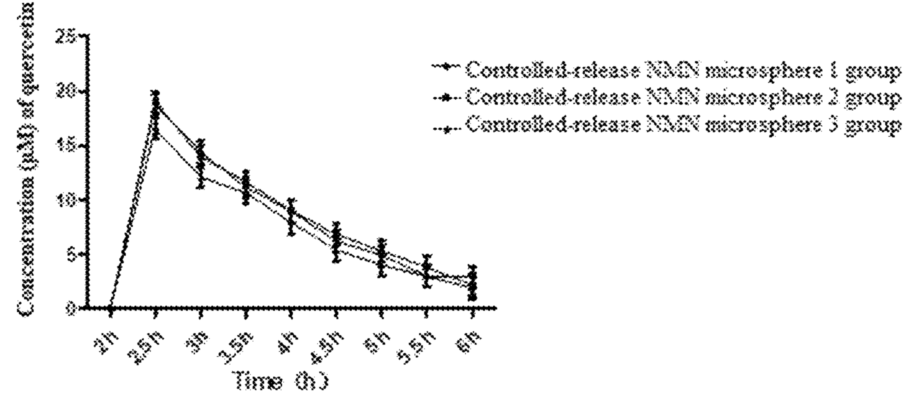
FIG. 2 is a diagram of a confirmatory experiment of release of quercetin in controlled-release NMN microsphere 1, 2, and 3 groups according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the content of NMN and the content of quercetin in the blood sample were respectively tested by high performance liquid chromatography (HPLC). The test results of 4 rats in each group were averaged. Results of the content of NMN in the blood samples are shown in Table 1 and FIG. 1, and results of the content of quercetin in the blood samples are shown in Table 2 and 5 FIG. 2. A time difference between a peak of the releasing of quercetin and a peak of the releasing of NMN in the controlled-release NMN microsphere 1 is about 1 h-2 h, a time difference between a peak of the releasing of quercetin and a peak of the releasing of NMN in the controlled-release NMN microsphere 2 is about 0.5 h-1.5 h, and a time difference between a peak of the releasing of quercetin and a peak of the releasing of NMN in the controlled-release NMN microsphere 3 is about 0-1 h.

TABLE 1

| Content (μM) of NMN in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NMN microsphere 1 group | 1390 | 1432 | 1490 | 1599 | 2307 | 1895 | 1621 | 1446 | 1404 |
| Group 2 | Controlled-release NMN microsphere 2 group | 1420 | 1498 | 1654 | 2735 | 1904 | 1712 | 1533 | 1402 | 1435 |
| Group 3 | Controlled-release NMN microsphere 3 group | 1330 | 1786 | 2301 | 1827 | 1634 | 1480 | 1329 | 1380 | 1347 |

TABLE 2

| Content (μM) of quercetin in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NMN microsphere 1 group | 0 | 18.76 | 14.38 | 11.19 | 8.94 | 6.23 | 4.9 | 3.01 | 2.89 |
| Group 2 | Controlled-release NMN microsphere 2 group | 0 | 19.01 | 13.99 | 11.67 | 9.02 | 6.85 | 5.31 | 3.82 | 2.18 |
| Group 3 | Controlled-release NMN microsphere 3 group | 0 | 16.59 | 12.09 | 10.66 | 7.92 | 5.41 | 4.01 | 2.97 | 1.94 |

Example 3 Confirmatory Experiment (Animal Experiment) of Significantly Increasing the Level of NAD+ by Controlled-Release NMN Microspheres 28 SD rats weighing about 200 g were purchased, and an experiment was carried out after one week of adaptive feeding. The 28 rats were divided into 7 groups, 4 rats per group (half male and half female). The rats in group 1 were not treated, the rats in group 2 were administered intragastrically with 100 mg/kg of NMN, the rats in group 3 were administered intragastrically with 10 mg/kg of quercetin, the rats in group 4 were administered intragastrically with 100 mg/kg of NMN and 10 mg/kg of quercetin at the same time, the rats in group 5 were administered intragastrically with the controlled-release microspheres 1 containing 100 mg/kg of NMN and 10 mg/kg of quercetin, the rats in group 6 were administered intragastrically with the controlled-release NMN microspheres 2 containing 100 mg/kg of NMN and 10 mg/kg of quercetin, and the rats in group 7 were administered intragastrically with the controlled-release NMN microspheres 3 containing 100 mg/kg of NMN and 10 mg/kg of quercetin.

Figure 3:
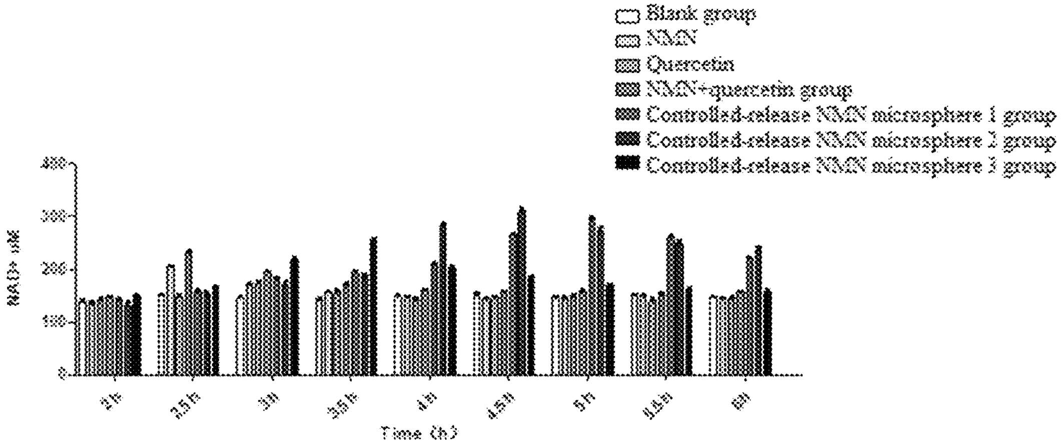
FIG. 3 is a diagram of a confirmatory experiment of increasing the level of NAD+ by controlled-release NMN microsphere 1, 2, and 3 groups according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the NAD+ level in the blood sample was tested by high performance liquid chromatography (HPLC). The test results of 4 rats in each group were averaged. Results are shown in Table 3 and FIG. 3. Compared with the blank group, all the intragastric treatment groups, that is, the NMN group, the quercetin group, the NMN+quercetin group, the controlled-release NMN microsphere 1 group, the controlled-release NMN microsphere 2 group, and the controlled-release NMN microsphere 3 group, can increase the level of NAD+ in the rat as time goes on. Among them, an NAD+ level increasing effect of combined administration of NMN and quercetin is superior to that of administration of NMN or quercetin alone. An NAD+ increasing effect of the controlled-release NMN microsphere 1, the controlled-release NMN microsphere 2 or the controlled-release NMN microsphere 3 is significantly superior to that of combined administration of NMN and quercetin. The NAD+ increasing effect of the controlled-release microsphere 2 is superior to that of the controlled-release NMN microsphere 1 or the controlled-release NMN microsphere 3. Different parameters are set in the preparation processes of the controlled-release NMN microsphere 1, the controlled-release NMN microsphere 2, and the controlled-release NMN microsphere 3, so the time intervals between release peaks of quercetin and release peaks of NMN in the microspheres are different. A time difference between a peak of the releasing of quercetin and a peak of the releasing of NMN in the controlled-release NMN microsphere 1 is 1 h-2 h, a time difference between a peak of the releasing of quercetin and a peak of the releasing of NMN in the controlled-release NMN microsphere 2 is 0.5 h-1.5 h, and a time difference between a peak of the releasing of quercetin and a peak of the releasing of NMN in the controlled-release NMN microsphere 3 is 0 h-1 h. The controlled-release NMN microspheres 1 and 2 have the best effect on increasing NAD+ in the rat.

Therefore, from the perspective of long-term results, the release of quercetin and NMN with time difference achieves a superior effect on increasing NAD+ in vivo compared to co-use of quercetin and NMN, and the optimal time difference is 0.5 h-1.5 h.

TABLE 3

| | | NAD+ level (μM) in blood | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 141 | 153 | 148 | 145 | 151 | 155 | 149 | 153 | 150 |
| Group 2 | NMN group | 139 | 207 | 173 | 159 | 150 | 145 | 148 | 152 | 147 |
| Group 3 | Quercetin group | 145 | 152 | 178 | 160 | 147 | 150 | 151 | 144 | 149 |
| Group 4 | NMN + quercetin group | 150 | 235 | 198 | 174 | 163 | 159 | 160 | 155 | 159 |
| Group 5 | Controlled-release NMN microsphere 1 group | 144 | 160 | 185 | 196 | 212 | 268 | 299 | 263 | 223 |
| Group 6 | Controlled-release NMN microsphere 2 group | 138 | 158 | 176 | 190 | 287 | 316 | 279 | 254 | 243 |
| Group 7 | Controlled-release NMN microsphere 3 group | 152 | 169 | 221 | 257 | 205 | 186 | 172 | 164 | 160 |

Example 4 Preparation of Controlled-Release NR Microspheres

The preparation process of the controlled-release NMN microsphere 2 in Example 1 was used, NMN was replaced with NR, quercetin was replaced with apigenin, and a controlled-release NR microsphere 4 was prepared. Specific steps were as follows:

(1) 200 g of NR and 50 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 20 g of apigenin, 172 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 5 Confirmatory Experiment (Animal Experiment) of Release of Controlled-Release NR Microspheres 4 SD rats (half male and half female) weighing about 200 g were purchased and administered intragastrically with the controlled-release NR microspheres 4. Doses of NR contained in the controlled-release NR microspheres administered intragastrically to the rats were the same, and intragastric administration doses of NR were all 100 mg/kg. Doses of apigenin contained in the controlled-release NR microspheres administered intragastrically to the rats were the same, and intragastric administration doses of apigenin were all 10 mg/kg.

Figure 4:
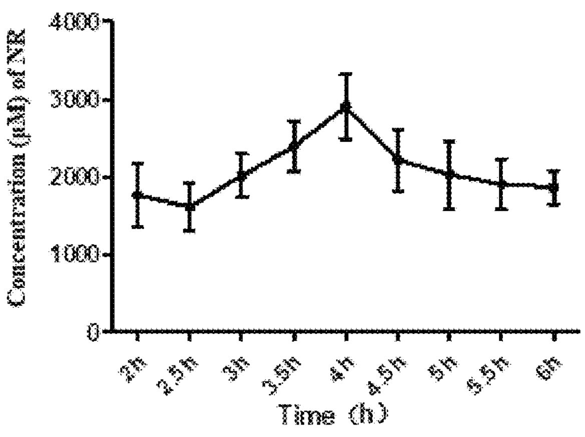
FIG. 4 is a diagram of a confirmatory experiment of release of NR in a controlled-release NR microsphere 4 group according to an embodiment of the present disclosure.
Figure 5:
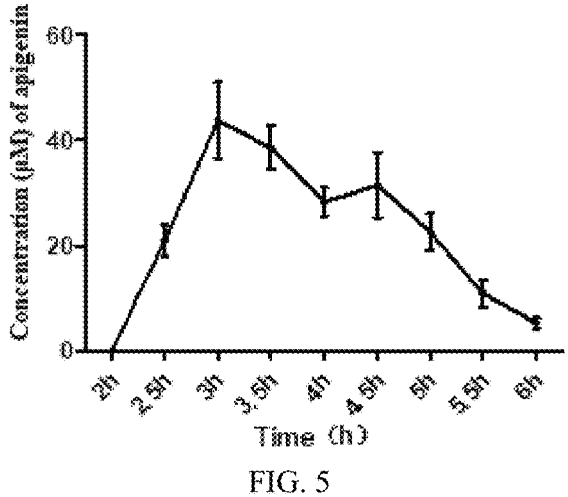
FIG. 5 is a diagram of a confirmatory experiment of release of apigenin in a controlled-release NR microsphere 4 group according to an embodiment of the present disclosure.

Blood was collected from each rat via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat at each time point was treated, the content of NR and the content of apigenin in the blood sample were respectively tested by high performance liquid chromatography (HPLC). The test results of the 4 rats were averaged. Results of the content of NR in blood are shown in Table 4 and FIG. 4, and results of the content of apigenin in blood are shown in Table 4 and FIG. 5. A time difference between a peak of the releasing of apigenin and a peak of the releasing of NR in the controlled-release NR microsphere 4 is about 0.5 h-1.5 h.

TABLE 4

| | 2 h | 2.5 h | 3 h | 3.5 h | 4 h | 4.5 h | 5 h | 5.5 h | 6 h |
|---|---|---|---|---|---|---|---|---|---|
| Content (μM) of NR in blood | 1760 | 1610 | 2016 | 2392 | 2901 | 2217 | 2029 | 1905 | 1866 |
| Content (μM) of apigenin in blood | 0 | 21.05 | 43.76 | 38.54 | 28.26 | 31.51 | 22.63 | 15.89 | 9.28 |

Example 6 Confirmatory Experiment (Animal Experiment) of Significantly Increasing the Level of NAD+ by Controlled-Release NR Microspheres 20 SD rats weighing about 200 g were purchased, and an experiment was carried out after one week of adaptive feeding. The 20 rats were divided into 5 groups, 4 rats per group (half male and half female). The rats in group 1 were not treated, the rats in group 2 were administered intragastrically with 100 mg/kg of NR, the rats in group 3 were administered intragastrically with 10 mg/kg of apigenin, the rats in group 4 were administered intragastrically with 100 mg/kg of NR and 10 mg/kg of apigenin at the same time, and the rats in group 5 were administered intragastrically with the controlled-release NR microspheres 4 containing 100 mg/kg of NR and 10 mg/kg of apigenin.

Figure 6:
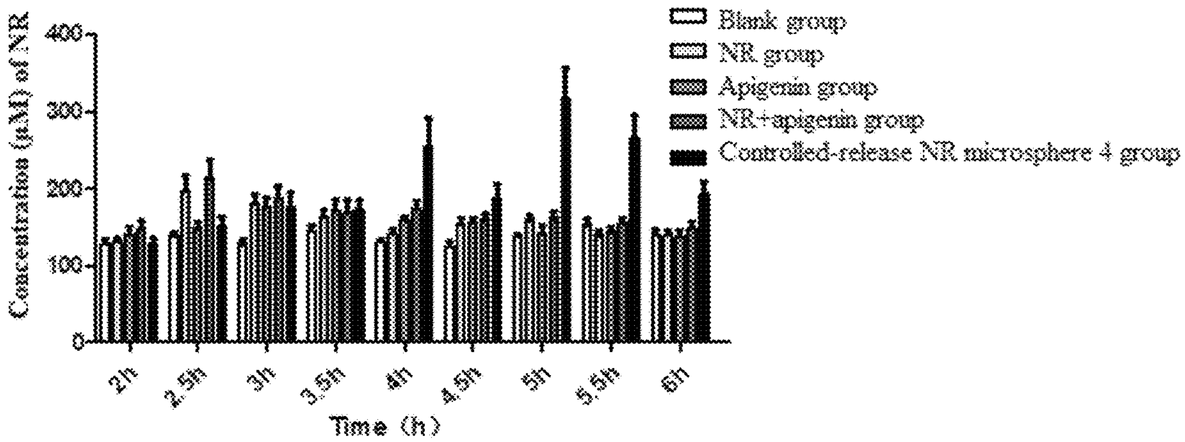
FIG. 6 is a diagram of a confirmatory experiment of increasing the level of NAD+ by a controlled-release NR microsphere 4 group according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat at each time point was treated, the NAD+ level in the blood sample was tested by high performance liquid chromatography (HPLC). The test results of 4 rats in each group were averaged. Results are shown in Table 5 and FIG. 6. Compared with the blank group, all the intragastric treatment groups, that is, the NR group, the apigenin group, the NR+apigenin group, and the controlled-release NR microsphere 4 group, can increase the level of NAD+ in the rat as time goes on. Among them, an NAD+ level raised of combined administration of NR and apigenin is superior to that of administration of NR or apigenin alone. An NAD+ level raised of the controlled-release NR microsphere 4 is significantly superior to that of combined administration of NR and apigenin.

Therefore, from the perspective of long-term results, the release of apigenin and NR with time difference achieves a superior effect on increasing NAD+ in vivo compared to co-use of apigenin and NR.

TABLE 5

| | | NAD+ level (μM) in blood | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 129 | 139 | 128 | 145 | 131 | 125 | 139 | 153 | 140 |
| Group 2 | NR group | 131 | 196 | 181 | 163 | 142 | 154 | 159 | 139 | 141 |
| Group 3 | Apigenin group | 141 | 148 | 176 | 171 | 160 | 156 | 143 | 144 | 138 |
| Group 4 | NR + apigenin group | 148 | 213 | 188 | 169 | 174 | 159 | 162 | 156 | 149 |
| Group 5 | Controlled-release NR microsphere 4 group | 128 | 151 | 176 | 173 | 254 | 188 | 316 | 265 | 193 |

Example 7 Preparation of Controlled-Release NMN Microspheres with Different Mass Ratios of Quercetin (a CD38 Inhibitor) to NMN 1. Preparation of a Controlled-Release NMN Microsphere 5:

The preparation process of the controlled-release NMN microsphere 2 in Example 1 was used, a mass ratio of quercetin (a CD38 inhibitor) to NMN was changed to 0.5:5, ratios of other excipients were unchanged, and a controlled-release NMN microsphere 5 was prepared. Specific steps were as follows:

(1) 5 g of NMN and 1.25 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 0.5 g of quercetin, 4.3 g of mannitol (a filler), and 0.15 g of L-HPC (a disintegrant) were taken and uniformly mixed, the mixture was added to a powder feeding system of a centrifugal granulator, 0.1 g of povidone K30 (a binder)

was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

2. Preparation of a Controlled-Release NMN Microsphere 6:

The preparation process of the controlled-release NMN microsphere 2 in Example 1 was used, a mass ratio of quercetin (a CD38 inhibitor) to NMN was changed to 30:300, ratios of other excipients were unchanged, and a controlled-release NMN microsphere 6 was prepared. Specific steps were as follows:

(1) 300 g of NMN and 75 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 30 g of quercetin, 258 g of mannitol (a filler), and 9 g of L-HPC (a disintegrant) were taken and uniformly mixed, the mixture was added to a powder feeding system of a centrifugal granulator, 3 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 8 Confirmatory Experiment (Animal Experiment) of Release of Controlled-Release NMN Microspheres with Different Mass Ratios of Quercetin (a CD38 Inhibitor) to NMN 12 SD rats weighing about 200 g were purchased, and an experiment was carried out after one week of adaptive feeding. The 12 rats were divided into 3 groups, 4 rats per group (half male and half female). The rats in group 1 were administered intragastrically with the controlled-release NMN microspheres 2, the rats in group 2 were administered intragastrically with the controlled-release NMN microspheres 5, and the rats in group 3 were administered intragastrically with the controlled-release NMN microspheres 6. Doses of NMN contained in the controlled-release NMN microspheres administered intragastrically to the rats in the groups were the same, and intragastric administration doses of NMN were all 100 mg/kg. Doses of quercetin contained in the controlled-release NMN microspheres administered intragastrically to the rats in the groups were the same, and intragastric administration doses of quercetin were all 10 mg/kg.

Figure 7:
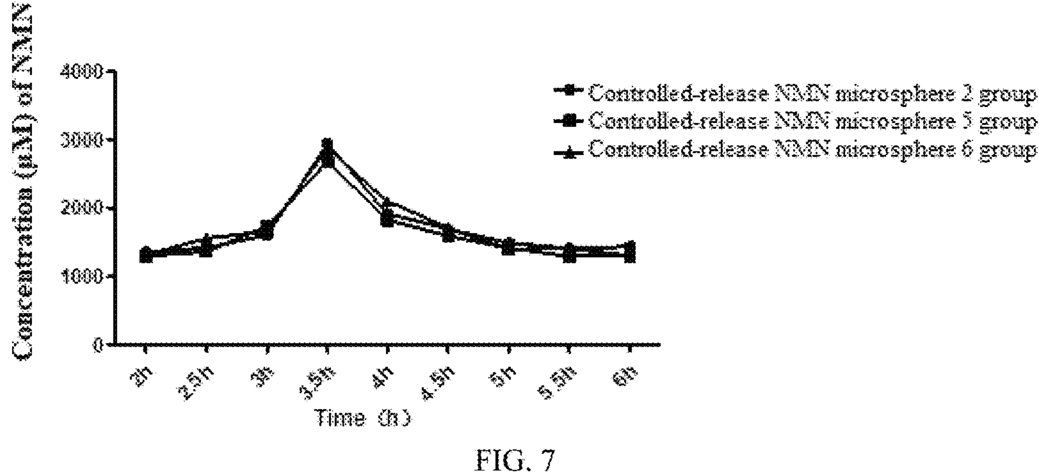
FIG. 7 is a diagram of a confirmatory experiment of release of NMN in controlled-release NMN microsphere 2, 5, and 6 groups according to an embodiment of the present disclosure.
Figure 8:
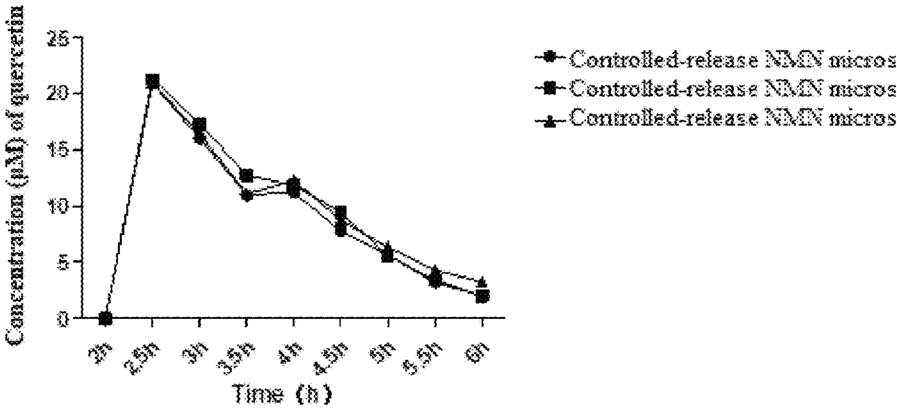
FIG. 8 is a diagram of a confirmatory experiment of release of quercetin in controlled-release NMN microsphere 2, 5, and 6 groups according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the content of NMN and the content of quercetin in the blood sample were respectively tested by high performance liquid chromatography (HPLC). The test results of 4 rats in each group were averaged. Results of the content of NMN in the blood samples are shown in Table 6 and FIG. 7, and results of the content of quercetin in the blood samples are shown in Table 7 and 5 FIG. 8. There are time differences between a peak of the releasing of quercetin and a peak of the releasing of NMN in the controlled-release NMN microsphere 2, the controlled-release NMN microsphere 5, and the controlled-release NMN microsphere 6 that are prepared based on different mass ratios of quercetin (the CD38 inhibitor) to NMN, and the time differences between a peak of the releasing of quercetin and a peak of the releasing of NMN in the three microspheres are consistent and are all about 0.5 h-1.5 h.

TABLE 6

| | Content (μM) of NMN in blood | | | | | | | | | |
|---|---|---|---|---|---|---|---|---|---|---|
| | Treament | 2 h | 2.5 h | 3 h | 3.5 h | 4 h | 4.5 h | 5 h | 5.5 h | 6 h |
| Group 1 | Controlled-release NMN microsphere 2 group | 1350 | 1418 | 1604 | 2940 | 1914 | 1691 | 1487 | 1412 | 1435 |
| Group 2 | Controlled-release NMN microsphere 5 group | 1298 | 1363 | 1733 | 2683 | 1822 | 1593 | 1415 | 1296 | 1300 |
| Group 3 | Controlled-release NMN microsphere 6 group | 1304 | 1559 | 1659 | 2875 | 2101 | 1706 | 1399 | 1415 | 1298 |

TABLE 7

| | Content (μM) of quercetin in blood | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NMN microsphere 2 group | 0 | 20.87 | 16.02 | 10.96 | 11.22 | 7.77 | 5.68 | 3.21 | 2.04 |
| Group 2 | Controlled-release NMN microsphere 5 group | 0 | 21.29 | 17.28 | 12.75 | 11.8 | 9.46 | 5.59 | 3.44 | 1.99 |
| Group 3 | Controlled-release NMN microsphere 6 group | 0 | 20.93 | 16.43 | 11.08 | 12.26 | 8.75 | 6.35 | 4.31 | 3.28 |

Example 9 Confirmatory Experiment (Animal Experiment) of Significantly Increasing the Level of NAD+ by Controlled-Release NMN Microspheres with Different Mass Ratios of Quercetin (a CD38 Inhibitor) to NMN 28 SD rats weighing about 200 g were purchased, and an experiment was carried out after one week of adaptive feeding. The 28 rats were divided into 7 groups, 4 rats per group (half male and half female). The rats in group 1 were not treated, the rats in group 2 were administered intragastrically with 100 mg/kg of NMN, the rats in group 3 were administered intragastrically with 10 mg/kg of quercetin, the rats in group 4 were administered intragastrically with 100 mg/kg of NMN and 10 mg/kg of quercetin at the same time, the rats in group 5 were administered intragastrically with the controlled-release NMN microspheres 2 containing 100 mg/kg of NMN and 10 mg/kg of quercetin, the rats in group 6 were administered intragastrically with the controlled-release NMN microspheres 5 containing 100 mg/kg of NMN and 10 mg/kg of quercetin, and the rats in group 7 were administered intragastrically with the controlled-release NMN microspheres 6 containing 100 mg/kg of NMN and 10 mg/kg of quercetin.

Figure 9:
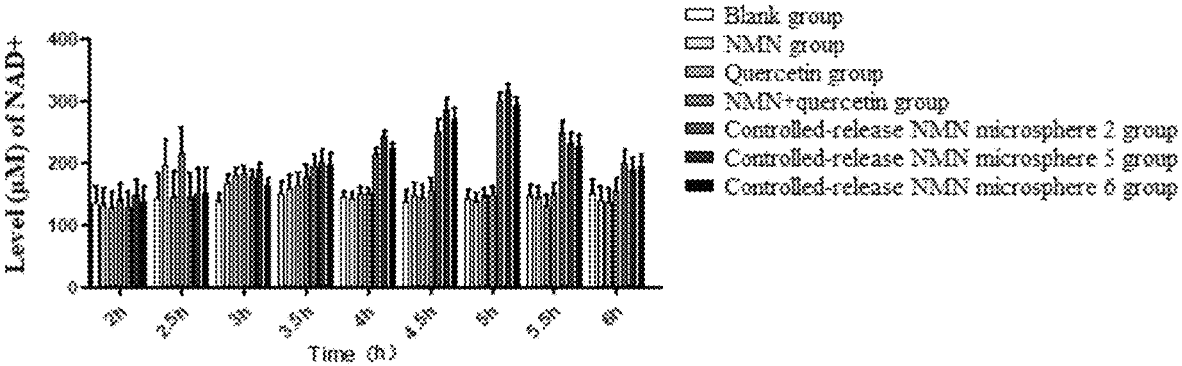
FIG. 9 is a diagram of a confirmatory experiment of increasing the level of NAD+ by controlled-release NMN microsphere 2, 5, and 6 groups according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the NAD+ level in the blood sample was tested by high performance liquid chromatography (HPLC). The test results of 4 rats in each group were averaged. Results are shown in Table 8 and FIG. 9. Compared with the blank group, all the intragastric treatment groups, that is, the NMN group, the quercetin group, the NMN+quercetin group, the controlled-release NMN microsphere 1 group, the controlled-release microsphere 2 group, and the controlled-release NMN microsphere 3 group, can increase the level of NAD+ in the rat at a certain time point as time goes on. Among them, an NAD+ level raised of combined administration of NMN and quercetin is superior to that of administration of NMN or quercetin alone. An NAD+ increasing effect of the controlled-release NMN microsphere 2, the controlled-release NMN microsphere 5 or the controlled-release NMN microsphere 6 is significantly superior to that of combined administration of NMN and quercetin. Moreover, there is no significant difference between the NAD+ increasing effects of the controlled-release NMN microsphere 2, the controlled-release NMN microsphere 5, and the controlled-release NMN microsphere 6. There are time differences between a peak of the releasing of quercetin and a peak of the releasing of NMN in the controlled-release NMN microsphere 2, the controlled-release NMN microsphere 5, and the controlled-release NMN microsphere 6 that are prepared based on difference mass ratios of quercetin (the CD38 inhibitor) to NMN, and the time differences between a peak of the releasing of quercetin and a peak of the releasing of NMN in the three microspheres are consistent and are all about 0.5-1.5 h. Moreover, there is no significant difference between the NAD+ increasing effects of the controlled-release NMN microsphere 2, the controlled-release NMN microsphere 5, and the controlled-release NMN microsphere 6.

Therefore, from the perspective of long-term results, if the mass ratio of quercetin (the CD38 inhibitor) to NMN is in the range of (0.5-30):(5-300), there is a significant time difference between a peak of the releasing of quercetin and a peak of the releasing of NMN in the microsphere, and the NAD+ increasing effect is significant. The mass ratio range is reasonable.

TABLE 8

| | NAD+ level (μM) in blood | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 135 | 144 | 139 | 150 | 145 | 137 | 143 | 147 | 152 |
| Group 2 | NMN group | 133 | 197 | 168 | 159 | 143 | 148 | 139 | 144 | 140 |
| Group 3 | Quercetin group | 127 | 146 | 180 | 164 | 151 | 144 | 147 | 130 | 137 |
| Group 4 | NMN + quercetin group | 141 | 216 | 183 | 177 | 150 | 156 | 148 | 149 | 155 |
| Group 5 | Controlled-release NMN microsphere 2 group | 129 | 144 | 176 | 194 | 215 | 250 | 301 | 249 | 199 |
| Group 6 | Controlled-release NMN microsphere 5 group | 148 | 150 | 188 | 202 | 243 | 287 | 316 | 231 | 187 |
| Group 7 | Controlled-release NMN microsphere 6 group | 136 | 151 | 164 | 195 | 222 | 269 | 294 | 227 | 193 |

Example 10 Preparation of Controlled-Release NR Microspheres with Different Mass Ratios of Apigenin (a CD38 Inhibitor) to NR 1. Preparation of a Controlled-Release NR Microsphere 7:

The preparation process of the controlled-release NR microsphere 4 in Example 4 was used, and a mass ratio of apigenin (a CD38 inhibitor) to NR was changed to 0.5:5, ratios of other excipients were unchanged, and a controlled-release NR microsphere 7 was prepared. Specific steps were as follows:

(1) 5 g of NR and 1.25 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3-5% of a mass concentration.

(2) 0.5 g of apigenin, 4.3 g of mannitol (a filler), and 0.15 g of L-HPC (a disintegrant) were taken and uniformly mixed, the mixture was added to a powder feeding system of a centrifugal granulator, 0.1 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

2. Preparation of a Controlled-Release NR Microsphere 8:

The preparation process of the controlled-release NR microsphere 4 in Example 4 was used, and a mass ratio of apigenin (a CD38 inhibitor) to NR was changed to 30:300, ratios of other excipients were unchanged, and a controlled-release NR microsphere 8 was prepared. Specific steps were as follows:

(1) 300 g of NR and 75 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 30 g of apigenin, 258 g of mannitol (a filler), and 9 g of L-HPC (a disintegrant) were taken and uniformly mixed, the mixture was added to a powder feeding system of a centrifugal granulator, 3 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 11 Confirmatory Experiment (Animal Experiment) of Release of Controlled-Release NR Microspheres with Different Mass Ratios of Apigenin (a CD38 Inhibitor) to NR 12 SD rats weighing about 200 g were purchased, and an experiment was carried out after one week of adaptive feeding. The 12 rats were divided into 3 groups, 4 rats per group (half male and half female). The rats in group 1 were administered intragastrically with the controlled-release NR microspheres 4, the rats in group 2 were administered intragastrically with the controlled-release NR microspheres 7, and the rats in group 3 were administered intragastrically with the controlled-release NR microspheres 8. Doses of NR contained in the controlled-release NR microspheres administered intragastrically to the rats in the groups were the same, and intragastric administration doses of NR were all 100 mg/kg. Doses of apigenin contained in the controlled-release NR microspheres administered intragastrically to the rats in the groups were the same, and intragastric administration doses of apigenin were all 10 mg/kg.

Figure 10:
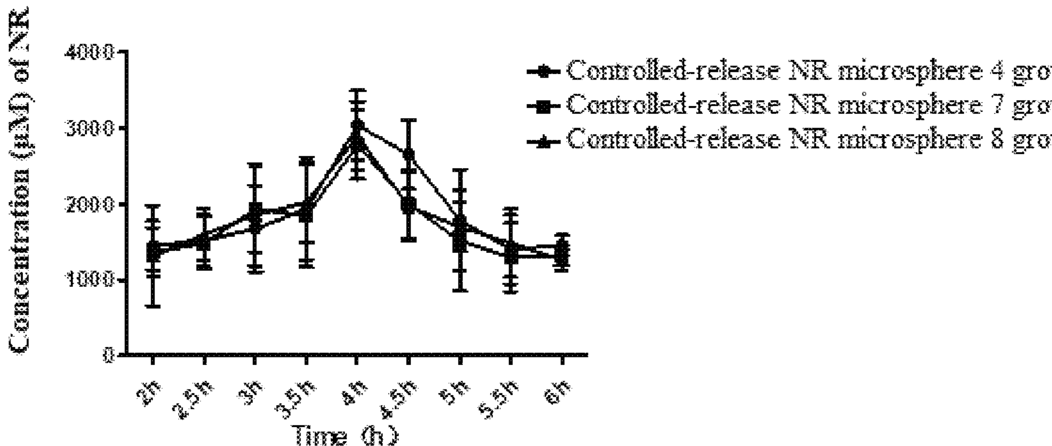
FIG. 10 is a diagram of a confirmatory experiment of release of NR in controlled-release NR microsphere 4, 7, and 8 groups according to an embodiment of the present disclosure.
Figure 11:
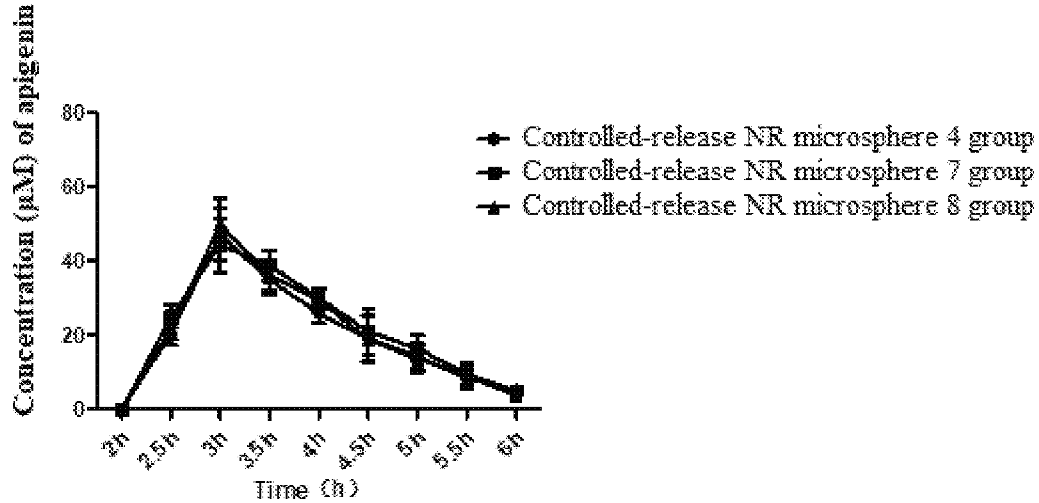
FIG. 11 is a diagram of a confirmatory experiment of release of apigenin in controlled-release NR microsphere 4, 7, and 8 groups according to an embodiment of the present disclosure.

Blood was collected from each rat in the groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat in the groups at each time point was treated, the content of NR and the content of apigenin in the blood sample were respectively tested by high performance liquid chromatography (HPLC). The test results of 4 rats in each group were averaged. Results of the content of NR in blood are shown in Table 9 and FIG. 10, and results of the content of apigenin in blood are shown in Table 10 and FIG. 11. There are time differences between a peak of the releasing of apigenin and a peak of the releasing of NR in the controlled-release NR microsphere 2, the controlled-release NR microsphere 7, and the controlled-release NR microsphere 8 that are prepared based on different mass ratios of apigenin (the CD38 inhibitor) to NR, and the time differences between a peak of the releasing of apigenin and a peak of the releasing of NR in the three microspheres are consistent and are all about 0.5 h-1.5 h.

TABLE 9

| | | Content (μM) of NR in blood | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NR microsphere 4 group | 1451 | 1518 | 1675 | 1934 | 3040 | 2656 | 1787 | 1400 | 1454 |
| Group 2 | Controlled-release NR microsphere 7 group | 1368 | 1482 | 1933 | 1847 | 2783 | 2003 | 1515 | 1296 | 1322 |
| Group 3 | Controlled-release NR microsphere 8 group | 1314 | 1601 | 1859 | 2023 | 2903 | 1967 | 1699 | 1486 | 1257 |

TABLE 10

| Content (μM) of apigenin in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NR microsphere 4 group | 0 | 20.45 | 47.23 | 35.19 | 26.01 | 19.2 | 14.34 | 8.56 | 5.31 |
| Group 2 | Controlled-release NR microsphere 7 group | 0 | 25.16 | 44.4 | 38.89 | 30.23 | 21.08 | 16.54 | 9.73 | 4.91 |
| Group 3 | Controlled-release NR microsphere 8 group | 0 | 22.11 | 50.08 | 36.39 | 29.69 | 18.98 | 13.72 | 9.35 | 3.84 |

Example 12 Confirmatory Experiment (Animal Experiment) of Significantly Increasing the Level of NAD+ by Controlled-Release NR Microspheres with Different Mass Ratios of Apigenin (a CD38 Inhibitor) to NR 28 SD rats weighing about 200 g were purchased, and an experiment was carried out after one week of adaptive feeding. The 28 rats were divided into 7 groups, 4 rats per group (half male and half female). The rats in group 1 were not treated, the rats in group 2 were administered intragastrically with 100 mg/kg of NR, the rats in group 3 were administered intragastrically with 10 mg/kg of apigenin, the rats in group 4 were administered intragastrically with 100 mg/kg of NR and 10 mg/kg of apigenin at the same time, the rats in group 5 were administered intragastrically with the controlled-release NR microspheres 4 containing 100 mg/kg of NR and 10 mg/kg of apigenin, the rats in group 6 were administered intragastrically with the controlled-release NR microspheres 7 containing 100 mg/kg of NR and 10 mg/kg of apigenin, and the rats in group 7 were administered intragastrically with the controlled-release NR microspheres 8 containing 100 mg/kg of NR and 10 mg/kg of apigenin.

Figure 12:
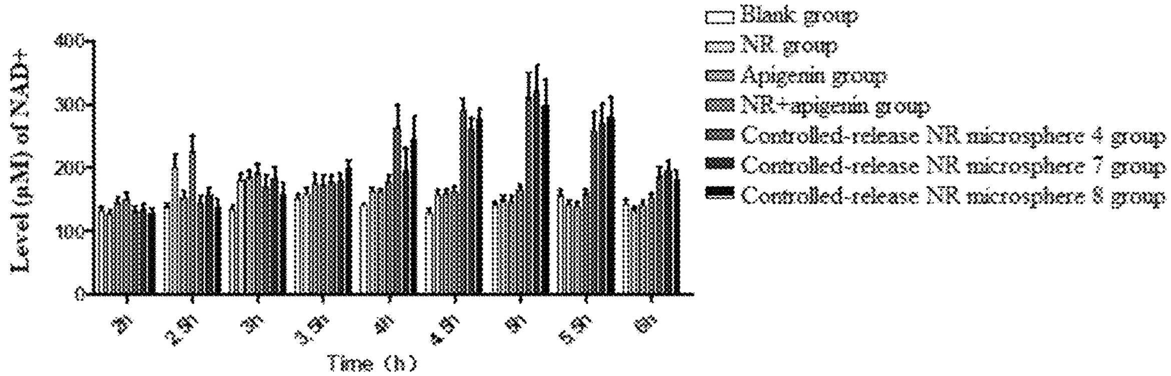
FIG. 12 is a diagram of a confirmatory experiment of increasing the level of NAD+ by controlled-release NR microsphere 4, 7, and 8 groups according to an embodiment of the present disclosure.

Blood was collected from each rat in the groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the NAD+ level in the blood sample was tested by high performance liquid chromatography (HPLC). The test results of 4 rats in each group were averaged. Results are shown in Table 11 and FIG. 12. Compared with the blank group, all the intragastric treatment groups, that is, the NR group, the apigenin group, the NR+apigenin group, the controlled-release NR microsphere 4 group, the controlled-release NR microsphere 7 group, and the controlled-release NR microsphere 8 group, can increase the level of NAD+ in the rat at a certain time point. An NAD+ level increasing effect of combined administration of NR and apigenin is superior to that of administration of NR or apigenin alone. An NAD+ increasing effect of the controlled-release NR microsphere 2, the controlled-release NR microsphere 7 or the controlled-release NR microsphere 8 is significantly superior to that of combined administration of NR and apigenin. Moreover, there is no significant difference between the NAD+ increasing effects of the controlled-release NR microsphere 2, the controlled-release NR microsphere 7, and the controlled-release NR microsphere 8. There are time differences between a peak of the releasing of apigenin and a peak of the releasing of NR in the controlled-release NR microsphere 2, the controlled-release NR microsphere 7, and the controlled-release NR microsphere 8 that are prepared based on different ratios of apigenin (the CD38 inhibitor) to NR, and the time differences between a peak of the releasing of apigenin and a peak of the releasing of NR in the three microspheres are consistent and are all 0.5-1.5 h. Moreover, there is no significant difference between the NAD+ increasing effects of the controlled-release NR microsphere 2, the controlled-release NR microsphere 7, and the controlled-release NR microsphere 8.

Therefore, if the mass ratio of apigenin (the CD38 inhibitor) to NR is in the range of (0.5-30):(5-300), there is a significant time difference between a peak of the releasing of apigenin and a peak of the releasing of NR in the microsphere, and the NAD+ increasing effect is significant. The mass ratio range is reasonable.

TABLE 11

| Content (μM) of NAD+ in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 133 | 139 | 134 | 151 | 141 | 129 | 143 | 156 | 143 |
| Group 2 | NR group | 128 | 200 | 180 | 159 | 162 | 157 | 149 | 142 | 134 |
| Group 3 | Apigenin group | 144 | 153 | 184 | 175 | 163 | 159 | 146 | 139 | 141 |
| Group 4 | NR + apigenin group | 150 | 225 | 191 | 172 | 178 | 162 | 165 | 159 | 152 |
| Group 5 | Controlled-release NR microsphere 4 group | 131 | 144 | 169 | 176 | 263 | 291 | 309 | 258 | 186 |
| Group 6 | Controlled-release NR microsphere 7 group | 134 | 157 | 182 | 179 | 194 | 260 | 321 | 271 | 196 |
| Group 7 | Controlled-release NR microsphere 8 group | 127 | 138 | 158 | 199 | 245 | 277 | 298 | 281 | 180 |

Example 13 Preparation of Controlled-Release NMN Microspheres with Different Ratios of Quercetin (a CD38 Inhibitor) to an Excipient and Different Mass Ratios of NMN to an Excipient 1. Preparation of a Controlled-Release NMN Microsphere 9:

The preparation process of the controlled-release NMN microsphere 2 in Example 1 was used, a mass ratio of quercetin (a CD38 inhibitor) to mannitol was changed to 1:5, a ratio of NMN to hydroxypropyl methylcellulose was changed to 5:1, and a controlled-release NMN microsphere 9 was prepared. Specific steps were as follows:

(1) 200 g of NMN and 40 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3-5% of a mass concentration.

(2) 20 g of quercetin, 100 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

2. Preparation of a Controlled-Release NMN Microsphere 10:

The preparation process of the controlled-release NMN microsphere 2 in Example 1 was used, a mass ratio of quercetin (a CD38 inhibitor) to mannitol was changed to 1:15, a ratio of NMN to hydroxypropyl methylcellulose was changed to 5:10, and a controlled-release NMN microsphere 10 was prepared. Specific steps were as follows:

(1) 200 g of NMN and 400 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3-5% of a mass concentration.

(2) 20 g of quercetin, 300 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 14 Confirmatory Experiment (Animal Experiment) of Release of Controlled-Release NMN Microspheres with Different Ratios of Quercetin (a CD38 Inhibitor) to an Excipient and Different Mass Ratios of NMN to an Excipient 12 SD rats weighing about 200 g were purchased, and an experiment was carried out after one week of adaptive feeding. The 12 rats were divided into 3 groups, 4 rats per group (half male and half female). The rats in group 1 were administered intragastrically with the controlled-release NMN microspheres 2, the rats in group 2 were administered intragastrically with the controlled-release NMN microspheres 9, and the rats in group 3 were administered intragastrically with the controlled-release NMN microspheres 10. Doses of NMN contained in the controlled-release NMN microspheres administered intragastrically to the rats in the groups were the same, and intragastric administration doses of NMN were all 100 mg/kg. Doses of quercetin contained in the controlled-release NMN microspheres administered intragastrically to the rats in the groups were the same, and intragastric administration doses of quercetin were all 10 mg/kg.

Figure 13:
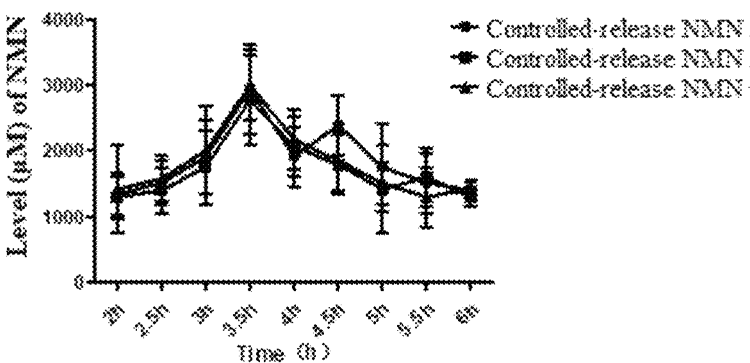
FIG. 13 is a diagram of a confirmatory experiment of release of NMN in controlled-release NMN microsphere 2, 9, and 10 groups according to an embodiment of the present disclosure.
Figure 14:
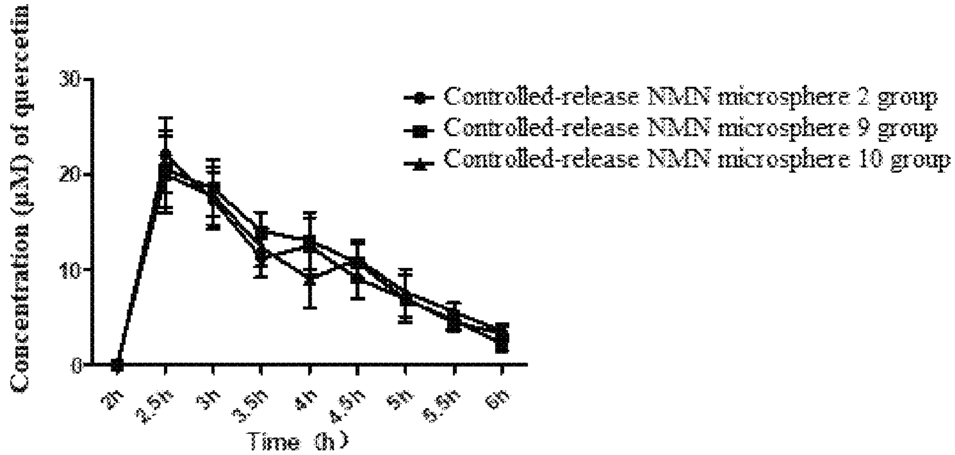
FIG. 14 is a diagram of a confirmatory experiment of release of quercetin in controlled-release NMN microsphere 2, 9, and 10 groups according to an embodiment of the present disclosure.

Blood was collected from each rat in the groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat in the groups at each time point was treated, the content of NMN and the content of quercetin in the blood sample were respectively tested by high performance liquid chromatography (HPLC). The test results of 4 rats in each group were averaged. Results of the content of NMN in the blood samples are shown in Table 12 and FIG. 13, and results of the content of quercetin in the blood samples are shown in Table 13 and FIG. 14. There are time differences between a peak of the releasing of quercetin and a peak of the releasing of NMN in the controlled-release NMN microsphere 2, the controlled-release NMN microsphere 9, and the controlled-release NMN microsphere 10 that are prepared based on different mass ratios of quercetin (the CD38 inhibitor) to a second excipient and different mass ratios of NMN to a first excipient, and the time differences between a peak of the releasing of quercetin and a peak of the releasing of NMN in the three microspheres are consistent and are all about 0.5 h-1.5 h.

TABLE 12

| | | Content (μM) of NMN in blood | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NMN microsphere 2 group | 1331 | 1518 | 1904 | 2940 | 1914 | 2391 | 1752 | 1510 | 1401 |
| Group 2 | Controlled-release NMN microsphere 9 group | 1287 | 1400 | 1752 | 2782 | 2065 | 1793 | 1415 | 1596 | 1300 |
| Group 3 | Controlled-release NMN microsphere 10 group | 1416 | 1576 | 2007 | 3006 | 2176 | 1852 | 1509 | 1298 | 1422 |

TABLE 13

| Content (μM) of quercetin in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NMN microsphere 2 group | 0 | 22.04 | 17.29 | 11.23 | 12.49 | 9.04 | 6.95 | 4.48 | 3.31 |
| Group 2 | Controlled-release NMN microsphere 9 group | 0 | 20.56 | 18.55 | 14.02 | 13.07 | 10.73 | 6.86 | 4.71 | 2.26 |
| Group 3 | Controlled-release NMN microsphere 10 group | 0 | 19.98 | 17.70 | 12.35 | 9.02 | 11.09 | 7.62 | 5.58 | 3.55 |

Example 15 Confirmatory Experiment (Animal Experiment) of Significantly Increasing the Level of NAD+ by Controlled-Release NMN Microspheres with Different Ratios of Quercetin (a CD38 Inhibitor) to an Excipient and Different Mass Ratios of NMN to an Excipient 28 SD rats weighing about 200 g were purchased, and an experiment was carried out after one week of adaptive feeding. The 28 rats were divided into 7 groups, 4 rats per group (half male and half female). The rats in group 1 were not treated, the rats in group 2 were administered intragastrically with 100 mg/kg of NMN, the rats in group 3 were administered intragastrically with 10 mg/kg of quercetin, the rats in group 4 were administered intragastrically with 100 mg/kg of NMN and 10 mg/kg quercetin at the same time, the rats in group 5 were administered intragastrically with the controlled-release NMN microspheres 2 containing 100 mg/kg of NMN and 10 mg/kg of quercetin, the rats in group 6 were administered intragastrically with the controlled-release NMN microspheres 9 containing 100 mg/kg of NMN and 10 mg/kg of quercetin, and the rats in group 7 were administered intragastrically with the controlled-release NMN microspheres 10 containing 100 mg/kg of NMN and 10 mg/kg of quercetin.

Figure 15:
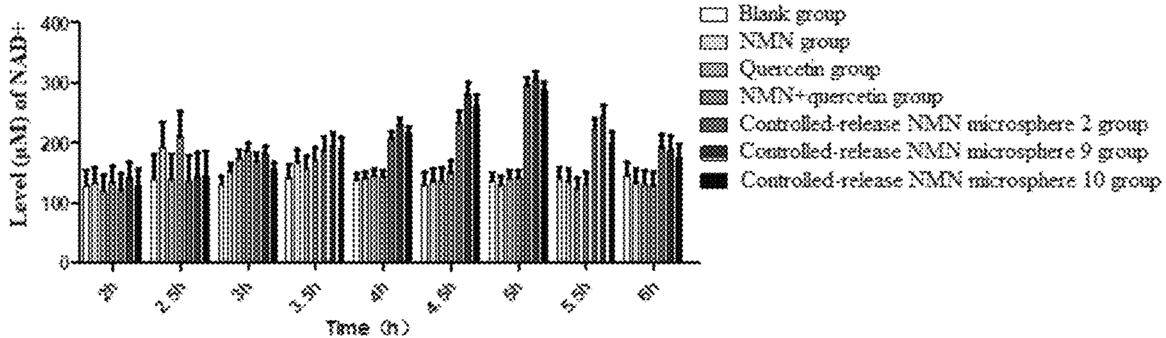
FIG. 15 is a diagram of a confirmatory experiment of increasing the level of NAD+ by controlled-release NMN microsphere 2, 9, and 10 groups according to an embodiment of the present disclosure.

Blood was collected from each rat in the groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat in the groups at each time point was treated, the NAD+ level in the blood sample was tested by high performance liquid chromatography (HPLC). The test results of 4 rats in each group were averaged. Results are shown in Table 14 and FIG. 15. Compared with the blank group, all the intragastric treatment groups, that is, the NMN group, the quercetin group, the NMN+quercetin group, the controlled-release NMN microsphere 2 group, the controlled-release NMN microsphere 9 group, and the controlled-release NMN microsphere 10 group, can increase the level of NAD+ in the rat at a certain time point. Among them, an NAD+ level increasing effect of combined administration of NMN and quercetin is superior to that of administration of NMN or quercetin alone. An NAD+ increasing effect of the controlled-release NMN microsphere 2, the controlled-release NMN microsphere 9 or the controlled-release NMN microsphere 10 is significantly superior to that of combined administration of NMN and quercetin. Moreover, there is no significant difference between the NAD+ increasing effects of the controlled-release NMN microsphere 2, the controlled-release NMN microsphere 9, and the controlled-release NMN microsphere 10. There are time differences between a peak of the releasing of quercetin and a peak of the releasing of NMN in the controlled-release NMN microsphere 2, the controlled-release NMN microsphere 9, and the controlled-release NMN microsphere 10 that are prepared based on different mass ratios of quercetin (the CD38 inhibitor) to the excipient and different mass ratios of NMN to the excipient, and the time differences between a peak of the releasing of quercetin and a peak of the releasing of NMN in the three microspheres are consistent and are all about 0.5-1.5 h. Moreover, there is no significant difference between the NAD+ increasing effects of the controlled-release NMN microsphere 2, the controlled-release NMN microsphere 9, and the controlled-release NMN microsphere 10.

Therefore, if the mass ratio of quercetin (the CD38 inhibitor) to a second excipient is 1 (part):(5-15) (parts), and the mass ratio of NMN to a first excipient is 5 (parts):(1-10) 5 (parts), there is a significant time difference between a peak of the releasing of quercetin and a peak of the releasing of NMN in the microsphere, and the NAD+ increasing effect is significant. The mass ratio ranges are reasonable.

TABLE 14

| NAD+ level (μM) in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 129 | 140 | 133 | 143 | 139 | 131 | 137 | 141 | 146 |
| Group 2 | NMN group | 134 | 193 | 153 | 168 | 142 | 137 | 131 | 138 | 134 |
| Group 3 | Quercetin group | 121 | 140 | 176 | 158 | 146 | 138 | 141 | 124 | 132 |
| Group 4 | NMN + quercetin group | 135 | 211 | 187 | 171 | 144 | 151 | 142 | 133 | 129 |
| Group 5 | Controlled-release NMN microsphere 2 group | 123 | 138 | 171 | 188 | 209 | 234 | 296 | 223 | 193 |
| Group 6 | Controlled-release NMN microsphere 9 group | 142 | 144 | 182 | 195 | 232 | 281 | 306 | 245 | 189 |
| Group 7 | Controlled-release NMN microsphere 10 group | 130 | 145 | 156 | 189 | 216 | 260 | 288 | 201 | 176 |

Example 16 Preparation of Controlled-Release NR Microspheres with Different Ratios of Apigenin (a CD38 Inhibitor) to an Excipient and Different Mass Ratios of NR to an Excipient 1. Preparation of a Controlled-Release NR Microsphere 11:

The preparation process of the controlled-release NR microsphere 4 in Example 4 was used, a mass ratio of apigenin (a CD38 inhibitor) to mannitol was changed to 1:5, a mass ratio of NR to hydroxypropyl methylcellulose was changed to 5:1, and a controlled-release NR microsphere 11 was prepared. Specific steps were as follows:

(1) 200 g of NR and 40 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 20 g of apigenin, 100 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

2. Preparation of a Controlled-Release NR Microsphere 12:

The preparation process of the controlled-release NMN microsphere 4 in Example 4 was used, a mass ratio of apigenin (a CD38 inhibitor) to mannitol was changed to 1:15, a ratio of NR to hydroxypropyl methylcellulose was changed to 5:10, and a controlled-release NMN microsphere 12 was prepared. Specific steps were as follows:

(1) 200 g of NR and 400 g of hydroxypropyl methylcellulose (an excipient for controlled release) were taken and uniformly mixed, and the mixture was prepared into a soft material with purified water in a wet type granulator. The soft material was placed into an extrusion spheronizator and extruded, a sieve plate with the diameter of 0.2 mm was used, and extruded pellets were rounded in the spheronizator and dried until the water content was 3%-5% of a mass concentration.

(2) 20 g of apigenin, 300 g of mannitol (a filler), and 6 g of L-HPC (a disintegrant) were taken and uniformly mixed, the mixture was added to a powder feeding system of a centrifugal granulator, 2 g of povidone K30 (a binder) was taken and prepared into an aqueous solution with a mass concentration of 5% with purified water, and the aqueous solution was added to a liquid spray system of the centrifugal granulator.

(3) The dried pellets were put into the centrifugal granulator, the device was started, the powder feeding system was turned on, and meanwhile, the liquid spray system was turned on to wrap the pellets. After being wrapped, the microspheres were dried.

Example 17 Confirmatory Experiment (Animal Experiment) of Release of Controlled-Release NR Microspheres with Different Ratios of Apigenin (a CD38 Inhibitor) to an Excipient and Different Mass Ratios of NR to an Excipient 12 SD rats weighing about 200 g were purchased, and an experiment was carried out after one week of adaptive feeding. The 12 rats were divided into 3 groups, 4 rats per group (half male and half female). The rats in group 1 were administered intragastrically with the controlled-release NR microspheres 2, the rats in group 2 were administered intragastrically with the controlled-release NR microspheres 11, and the rats in group 3 were administered intragastrically with the controlled-release NR microspheres 12. Doses of NR contained in the controlled-release NR microspheres administered intragastrically to the rats in each groups were the same, and intragastric administration doses of NR were all 100 mg/kg. Doses of apigenin contained in the controlled-release NR microspheres administered intragastrically to the rats in each groups were the same, and intragastric administration doses of apigenin were all 10 mg/kg.

Figure 16:
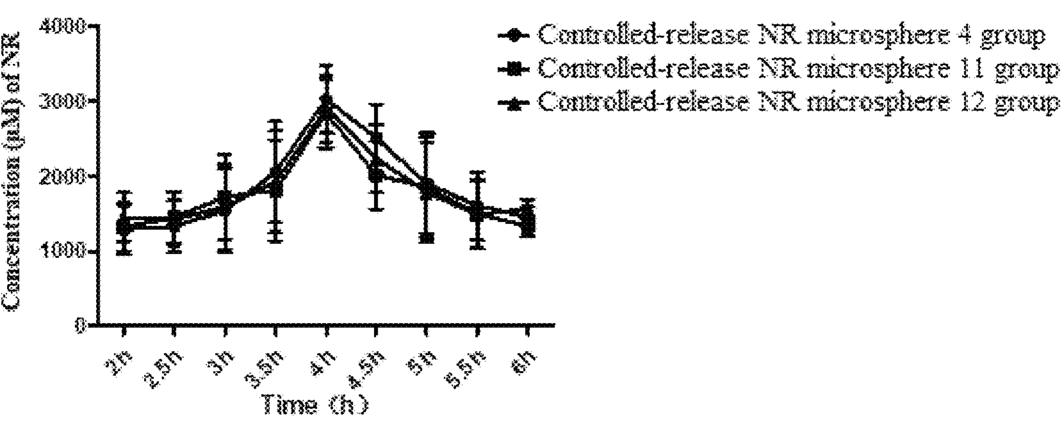
FIG. 16 is a diagram of a confirmatory experiment of release of NR in controlled-release NR microsphere 4, 11, and 12 groups according to an embodiment of the present disclosure.
Figure 17:
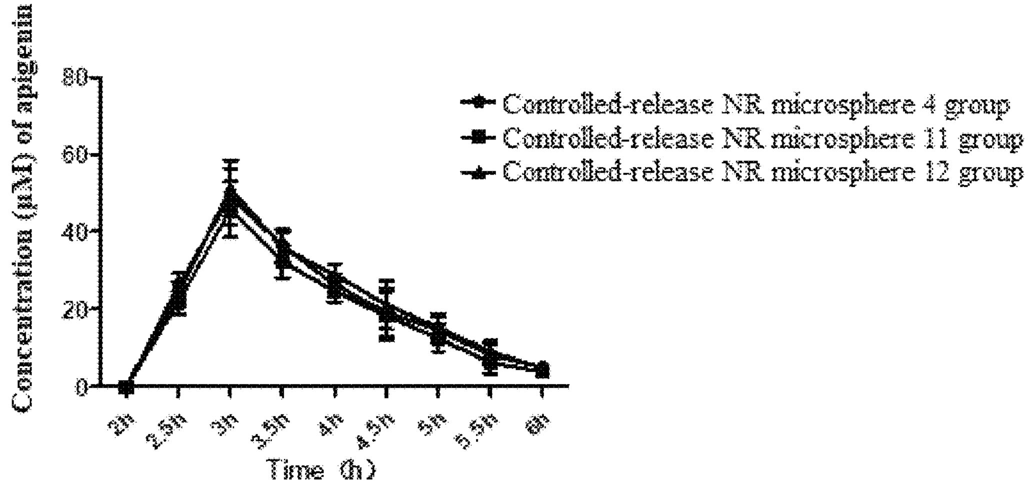
FIG. 17 is a diagram of a confirmatory experiment of release of apigenin in controlled-release NR microsphere 4, 11, and 12 groups according to an embodiment of the present disclosure.

Blood was collected from the rat in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from the rat in each groups at each time point was treated, the content of NR and the content of apigenin in the blood sample were respectively tested by high performance liquid chromatography (HPLC). The test results of 4 rats in each group were averaged. Results of the content of NR in blood are shown in Table 15 and FIG. 16, and results of the content of apigenin in blood are shown in Table 16 and FIG. 17. There are time differences between a peak of the releasing of apigenin and a peak of the releasing NR in the controlled-release NR microsphere 2, the controlled-release NR microsphere 11, and the controlled-release NR microsphere 12 that are prepared based on different mass ratios of apigenin (the CD38 inhibitor) to the excipient and different mass ratios of NR to the excipient, and the time differences between a peak of the releasing of apigenin and a peak of the releasing NR in the three microspheres are consistent and are all about 0.5 h to 1.5 h.

TABLE 15

| | | Content (μM) of NR in blood | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NR microsphere 4 group | 1287 | 1329 | 1544 | 2053 | 3026 | 2508 | 1902 | 1600 | 1454 |
| Group 2 | Controlled-release NR microsphere 11 group | 1320 | 1445 | 1723 | 1809 | 2835 | 2014 | 1851 | 1496 | 1322 |
| Group 3 | Controlled-release NR microsphere 12 group | 1451 | 1425 | 1588 | 1924 | 2899 | 2234 | 1786 | 1486 | 1557 |

TABLE 16

| Content (μM) of apigenin in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Controlled-release NR microsphere 4 group | 0 | 26.34 | 49.11 | 36.44 | 26.37 | 19.22 | 14.71 | 8.21 | 5.12 |
| Group 2 | Controlled-release NR microsphere 11 group | 0 | 21.82 | 45.92 | 32.17 | 24.76 | 18.29 | 12.66 | 6.32 | 3.91 |
| Group 3 | Controlled-release NR microsphere 12 group | 0 | 24.09 | 51.28 | 35.82 | 29.02 | 21.23 | 15.31 | 9.09 | 4.87 |

Example 18 Confirmatory Experiment (Animal Experiment) of Significantly Increasing the Level of NAD+ by Controlled-Release NR Microspheres with Different Ratios of Apigenin (a CD38 Inhibitor) to an Excipient and Different Mass Ratios of NR to an Excipient 28 SD rats weighing about 200 g were purchased, and an experiment was carried out after one week of adaptive feeding. The 28 rats were divided into 7 groups, 4 rats per group (half male and half female). The rats in group 1 were not treated, the rats in group 2 were administered intragastrically with 100 mg/kg of NR, the rats in group 3 were administered intragastrically with 10 mg/kg of apigenin, the rats in group 4 were administered intragastrically with 100 mg/kg of NR and 10 mg/kg of apigenin, the rats in group 5 were administered intragastrically with the controlled-release NR microspheres 2 containing 100 mg/kg of NR and 10 mg/kg of apigenin, the rats in group 6 were administered intragastrically with the controlled-release NR microspheres 11 containing 100 mg/kg of NR and 10 mg/kg of apigenin, and the rats in group 7 were administered intragastrically with the controlled-release NR microspheres 12 containing 100 mg/kg of NR and 10 mg/kg of apigenin.

Figure 18:
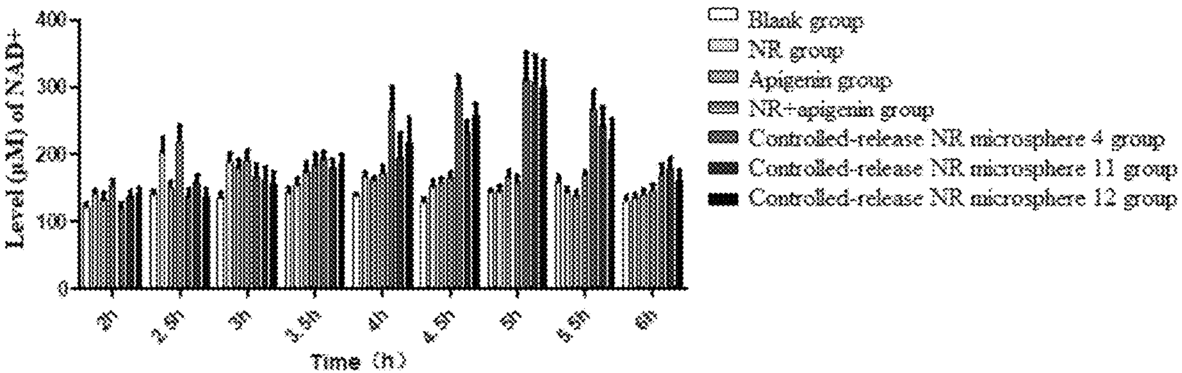
FIG. 18 is a diagram of a confirmatory experiment of increasing the level of NAD+ by controlled-release NR microsphere 4, 11, and 12 groups according to an embodiment of the present disclosure.

Blood was collected from rat the in each groups via the tail vein at time points of 2 h, 2.5 h, 3 h, 3.5 h, 4 h, 4.5 h, 5 h, 5.5 h, and 6 h, respectively, after intragastric administration of corresponding microspheres, and 0.1 mL of blood was collected each time by each rat. After the vein blood collected from each rat in the groups at each time point was treated, the NAD+ level in the blood sample was tested by high performance liquid chromatography (HPLC). The test results of 4 rats in each group were averaged. Results are shown in Table 17 and FIG. 18. Compared with the blank group, all the intragastric treatment groups, that is, the NR group, the apigenin group, the NR+apigenin group, the controlled-release NR microsphere 4 group, the controlled-release NR microsphere 11 group, and the controlled-release NR microsphere 12 group, can increase the level of NAD+ in the rat at a certain time point. Among them, an NAD+ level increasing effect of combined administration of NR and apigenin is superior to that of administration of NR or apigenin alone. An NAD+ increasing effect of the controlled-release NR microsphere 4, the controlled-release NR microsphere 11 or the controlled-release NR microsphere 12 is significantly superior to that of combined administration of NR and apigenin. Moreover, there is no significant difference between the NAD+ increasing effects of the controlled-release NR microsphere 2, the controlled-release NR microsphere 11, and the controlled-release NR microsphere 12. There are time differences between a peak of the releasing of apigenin and a peak of the releasing NR in the controlled-release NR microsphere 4, the controlled-release NR microsphere 11, and the controlled-release NR microsphere 12 that are prepared based on different mass ratios of apigenin (the CD38 inhibitor) to the excipient and different mass ratios of NR to the excipient, and the time differences between a peak of the releasing of apigenin and a peak of the releasing NR in the three microspheres are consistent and are all about 0.5 h to 1.5 h. Moreover, there is no significant difference between the NAD+ increasing effects of the controlled-release NR microsphere 4, the controlled-release NR microsphere 11, and the controlled-release NR microsphere 12.

Therefore, if the mass ratio of apigenin (the CD38 inhibitor) to a second excipient is 1 (part):(5-15) (parts), and the mass ratio of NR to a first excipient is 5 (parts):(1-10) (parts), there is a significant time difference between a peak of the releasing of apigenin and a peak of the releasing NR in the microsphere, and the NAD+ increasing effect is significant. The mass ratio ranges are reasonable.

TABLE 17

| NAD+ level (μM) in blood | | | | | | | | | | |
|---|---|---|---|---|---|---|---|---|---|---|
| | Treatment | 2 h | 2.5 h | 3 h | 3.5 h | 4 h | 4.5 h | 5 h | 5.5 h | 6 h |
| Group 1 | Blank group | 121 | 140 | 135 | 142 | 137 | 128 | 144 | 158 | 130 |
| Group 2 | NR group | 142 | 203 | 188 | 154 | 167 | 152 | 145 | 144 | 135 |
| Group 3 | Apigenin group | 132 | 150 | 179 | 173 | 161 | 157 | 166 | 138 | 140 |
| Group 4 | NR + apigenin group | 151 | 218 | 190 | 184 | 171 | 164 | 158 | 169 | 146 |
| Group 5 | Controlled-release NR microsphere 4 group | 119 | 136 | 166 | 192 | 264 | 298 | 310 | 266 | 169 |
| Group 6 | Controlled-release NR microsphere 11 group | 136 | 157 | 161 | 179 | 193 | 231 | 307 | 240 | 177 |
| Group 7 | Controlled-release NR microsphere 12 group | 141 | 136 | 154 | 187 | 216 | 257 | 299 | 221 | 160 |

In the description, the reference term "an embodiment", "some embodiments", "example", "specific example", "some examples" or the like is intended to indicate that a specific feature, structure, material or characteristic described with reference to the embodiment or example is included in at least one embodiment or example of the present disclosure. In the description, the schematic expressions of the foregoing terms are not necessarily directed to the same embodiment or example. Moreover, the specific feature, structure, material or characteristic described may be combined in any one or more embodiments or examples in an appropriate manner. In addition, those skilled in the art may combine and integrate different embodiments or examples and features of different embodiments or examples described in the description without conflicting with each other.

Although the embodiments of the present disclosure have been illustrated and described above. It may be understood that the foregoing embodiments are exemplary and should not be construed as limiting the present disclosure. Those of ordinary skill in the art may make changes, modifications, substitutions, and variations to the foregoing embodiments within the scope of the present disclosure.

What is claimed is:

1. A method for improving bioavailability of an NAD+ derivative, comprising: administering microspheres into a subject, wherein the microspheres each comprise:

a) a pellet core comprising the NAD+ derivative and an excipient for controlled release selected from at least one of: a hydrophilic gel material and a bioerodible material; and b) a coating comprising a CD38 inhibitor and a filler;

wherein an outer surface of the pellet core is wrapped with the coating;

wherein the CD38 inhibitor is selected from at least one of: quercetin, apigenin, resveratrol, grape seed extract, strawberry extract, and cocoa extract;

wherein the NAD+ derivative is selected from at least one of: nicotinamide mononucleotide (NMN), nicotinamide riboside (NR), nicotinamide (NAM), and nicotinamide adenine dinucleotide (NADH); and wherein the CD38 inhibitor and the NAD+ derivative in the microsphere are released stepwise in such a manner that the CD38 inhibitor releases first and then the NAD+ derivative releases.

2. The method according to claim 1, wherein a time difference between a timepoint at which the releasing of the NAD+ derivative reaches the maximum and a timepoint at which the releasing of the CD38 inhibitor reaches the maximum is at least 0.5 h.

3. The method according to claim 1, wherein a time difference between a timepoint at which the releasing of the CD38 inhibitor reaches the maximum and a timepoint at which the releasing of the NAD+ derivative reaches the maximum is 0.5 h-4 h.

4. The method according to claim 1, wherein a mass ratio of the CD38 inhibitor to the NAD+ derivative is (0.5-30): (5-300).

5. The method according to claim 1, wherein the hydrophilic gel material is selected from at least one of sodium carboxymethyl cellulose (CMC-Na); hydroxypropyl cellulose; hydroxypropyl methylcellulose (HPMC); povidone (PVP); ethyl cellulose (EC); polyethylene glycol; microcrystalline cellulose; carbomer (acrylic resin); alginate; and deacetylated chitosan (chitosan); and wherein the bioerodible material is selected from at least one of beeswax; carnauba wax; stearyl alcohol; glycerol monostearate; cetyl alcohol; stearyl alcohol; octacosanol; and rice bran fatty alkanol.

6. The method according to claim 1, wherein the filler is selected from at least one of: glucose, sucrose, mannitol, xylitol, erythritol, and sodium bicarbonate.

7. The method according to claim 1, wherein a mass ratio of the NAD+ derivative to the excipient for controlled release is 5:1 to 5:10; and a mass ratio of the CD38 inhibitor to the filler is 1:5 to 1:15.

* * * * *